United States Patent

Berryman et al.

[11] Patent Number: 6,124,291
[45] Date of Patent: Sep. 26, 2000

[54] PYRROLO[1,2-A]PYRAZINE-1,4-DIONE SERINE PROTEASE INHIBITORS

[75] Inventors: Kent A. Berryman; Annette M. Doherty, both of Ann Arbor; Jeremy J. Edmunds, Ypsilanti, all of Mich.; M. Arshad Siddiqui, St-Laurent, Canada

[73] Assignee: Warner-Lambert Company, Morris Plains, N.J.

[21] Appl. No.: 09/171,863

[22] PCT Filed: Jun. 10, 1997

[86] PCT No.: PCT/US97/09832

§ 371 Date: Oct. 27, 1998

§ 102(e) Date: Oct. 27, 1998

[87] PCT Pub. No.: WO97/48706

PCT Pub. Date: Dec. 24, 1997

Related U.S. Application Data

[60] Provisional application No. 60/019,989, Jun. 18, 1996.

[51] Int. Cl.[7] .................. C07D 401/12; C07D 403/12; C07D 241/38; A61K 31/498
[52] U.S. Cl. ............................. 514/249; 544/349
[58] Field of Search ..................... 544/229, 337, 544/349, 243, 295; 540/599; 514/212, 249, 80

[56] References Cited

U.S. PATENT DOCUMENTS 4,929,270  5/1990  Cardellina, II et al. ................. 71/92
5,543,521  8/1996  Chan et al. ............................. 544/349

FOREIGN PATENT DOCUMENTS 2354056  5/1974  Germany .
9323404  11/1993  WIPO .
9619483  6/1996  WIPO .

Primary Examiner—John M. Ford
Attorney, Agent, or Firm—Charles W. Ashbrook

[57] ABSTRACT

This invention relates to pyrrolo[1,2-a]pyrazine-1,4-diones of general formula:

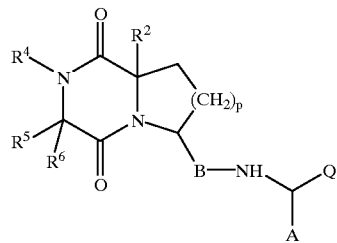

wherein B is carbonyl or methylene, $R^2$, $R^4$, $R^5$, and $R^6$ are hydrogen, alkyl, or substituted alkyl, A is a basic group, and Q is hydrogen or a keto heterocycle group.

The compounds are inhibitors of serine proteases, typically thrombin, Factor Xa, and Factor VIIa, and are useful for treating and preventing thrombotic disorders.

4 Claims, No Drawings

PYRROLO[1,2-A]PYRAZINE-1,4-DIONE SERINE PROTEASE INHIBITORS

This application was filed under 35 USC 371 from PCT/US97/098032, which was filed Jun. 10, 1997, which claimed priority to provisional U.S. application Ser. No. 60/019,989, which was filed Jun. 18, 1996.

FIELD OF THE INVENTION

This invention relates to the compounds useful for the treatment of thrombotic disorders by the inhibition of serine proteases, typically thrombin, Factor Xa, and/or Factor VIIa. The compounds are characterized as pyrrolo[1,2-a]pyrazine-1,4-dione derivatives.

BACKGROUND OF THE INVENTION

Inordinate thrombus formation on blood vessel walls precipitates acute cardiovascular disease states that are the chief cause of death in economically developed societies. Plasma proteins such as fibrinogen, proteases, and cellular receptors participating in hemostasis have emerged as important factors that play a role in acute and chronic coronary disease, as well as cerebral artery disease, by contributing to the formation of thrombus or blood clots that effectively diminish normal blood flow and supply. Vascular aberrations stemming from primary pathologic states such as hypertension, rupture of atherosclerotic plaques, or denuded endothelium activate biochemical cascades that serve to respond and repair the injury site. Thrombin is a key regulatory enzyme in the coagulation cascade; it serves a pluralistic role as both a positive and negative feedback regulator. However, in pathologic conditions the former is amplified through catalytic activation of cofactors required for thrombin generation as well as activation of Factor XIII necessary for fibrin cross-linking and stabilization.

In addition to its direct effect on hemostasis, thrombin exerts direct effects on diverse cell types that support and amplify pathogenesis of arterial thrombus disease. The enzyme is the strongest activator of platelets, causing them to aggregate and release substances that further propagate the thrombotic cycle. Platelets in a fibrin mesh comprise the principal framework of a white thrombus. Thrombin also exerts direct effects on endothelial cells, causing release of vasoconstrictor substances and translocation of adhesion molecules that become sites for attachment of immune cells. In addition, the enzyme causes mitogenesis of smooth muscle cells and proliferation of fibroblasts. From this analysis, it is apparent that inhibition of thrombin activity constitutes a viable therapeutic approach towards the attenuation of proliferative events associated with thrombosis.

The principal endogenous neutralizing factor for thrombin activity in mammals is Antithrombin III (ATIII), a circulating plasma macroglobulin having low affinity for the enzyme. Heparin exerts clinical efficacy in venous thrombosis by enhancing ATIII/thrombin binding through catalysis. However, heparin also catalyzes inhibition of other proteases in the coagulation cascade, and its efficacy in platelet-dependent thrombosis is largely reduced or abrogated due to inaccessibility of thrombus-bound enzyme. Adverse side effects such as thrombocytopenia, osteoporosis, and triglyceridemnia have been observed following prolonged treatment with heparin.

Hirudin, derived from the glandular secretions of the leech *hirido medicinalis*, is one of the high molecular weight natural anticoagulant protein inhibitors of thrombin activity (Markwardt F., *Cardiovascular Drug Reviews*, 1992; 10:211). It is a biopharmaceutical that has demonstrated efficacy in experimental and clinical thrombosis. A potential drawback to the use of Hirudin as a therapeutic agent is likely antigenicity and lack of an effective method of neutralization, especially in view of its extremely tight binding characteristics toward thrombin. The exceedingly high affinity for thrombin is unique and is attributed to a simultaneous interaction with the catalytic site as well as a distal "anion binding exosite" on the enzyme.

Thrombin activity can also be abrogated by Hirudin-like molecules such as hirulog (Maraganore J. M., et al., *Biochemistry*, 1990; 29:7095) or hirutonin peptides (DiMaio J., et al., *J. Med. Chem.*, 1992; 35:3331).

Thrombin activity can also be inhibited by low molecular weight compounds that compete with fibrinogen for thrombin's catalytic site, thereby inhibiting proteolysis of that protein or other protein substrates such as the thrombin receptor. A common strategy for designing enzyme inhibitory compounds relies on mimicking the specificity inherent in the primary and secondary structure of the enzyme's natural substrate. Thus, Blomback, et al., first designed a thrombin inhibitor that was modeled upon the partial sequence of the fibrinogen chain comprising its proteolytically susceptible region (Blomback, et al., *J. Clin. Lab. Invest.*, 1969;24:59). Systematic replacement of amino acids has led to optimization of the tripeptidyl inhibitory sequence exemplified by the peptide (D)-Phe-Pro-Arg, which corresponds to interactions within the $S_3\_S_2\_S_1$ local binding sites on thrombin (Bajusz S., et al., Peptides: Chemistry Structure and Biology. In: Walter R., Meienhofer J., eds. Proceedings of the Fourth American Peptide Symposium. *Ann Arbor Science Publishers Inc*, 1975:306).

Bajusz, et al., have also reported related compounds such as (D)Phe-Pro-Arg-(CO)H (GYKI-14166) and (D)MePhe-Pro-Arg-(CO)H (GYKI-14766) (Peptides-Synthesis, Structure and Function. In: Rich D. H. and Gross E., eds. Proceedings of the Seventh American Peptide Symposium. *Pierce Chemical Company*, 1981:417). These tripeptidyl aldehydes are effective thrombin inhibitors both in vitro and in vivo. In the case of both GYKI-14166 and GYKI-14766, the aldehyde group is presumed to contribute strongly to inhibitory activity in view of its chemical reactivity toward thrombin's catalytic $Ser_{195}$ residue, generating a hemiacetal intermediate.

Related work in the area of thrombin inhibitory activity has exploited the basic recognition binding motif engendered by the tripeptide (D)Phe-Pro-Arg while incorporating various functional or reactive groups in the locus corresponding to the putative scissile bond (ie, $P_1$–$P_1'$).

In U.S. Pat. No. 4,318,904, Shaw reports chloromethyl-ketones (PPACK) that are reactive towards $Ser_{195}$ and $His_{57}$. These two residues comprise part of thrombin's catalytic triad (Bode W., et al., *EMBO Journal*, 1989; 8:3467).

Other examples of thrombin inhibitors bearing the (D)Phe-Pro-Arg general motif are those incorporating COOH-terminal boroarginine variants such as boronic acids or boronates (Kettner C., et al., *J. Biol. Chem.*, 1993; 268:4734).

Still other congeners of this motif are those bearing phosphonates (Wang C-L J., *Tetrahedron Letters*, 1992; 33:7667) and a-Keto esters (Iwanowicz E. J., et al., *Bioorganic and Medicinal Chemistry Letters*, 1992; 12:1607).

Neises B, et al., have described a trichloromethyl ketone thrombin inhibitor (MDL-73756) and Attenburger J. M., et al., have revealed a related difluoro alkyl amide ketone (*Tetrahedron Letters*, 1991; 32:7255).

Maraganore, et al. (European Patent 0,333,356; WO 91/02750; U.S. Pat. No. 5,196,404), disclose a series of thrombin inhibitors that incorporate the D-Phe-Pro moiety and hypothesize that this preferred structure fits well within the groove adjacent to the active site of thrombin. Variations on these inhibitors are essentially linear or cyclic peptides built upon the D-Phe-Pro moiety.

Another series of patents and patent applications have described attempts to develop effective inhibitors against thrombosis by using alpha-ketoamides and peptide aldehyde analogs (EP 0333356; WO 93/15756; WO 93/22344; WO 94/08941; WO 94/17817).

Still others have focused their attention on peptides, peptide derivatives, peptidic alcohols, or cyclic peptides as antithrombotic agents (WO 93/22344; EP 0276014; EP 0341607; EP 0291982). Others have examined amidine sulfonic acid moieties to achieve this same end (U.S. Pat. No. 4,781,866), while yet others have examined para- or meta-substituted phenylalanine derivatives (WO 92/08709; WO 92/6549).

A series of Mitsubishi patents and patent applications have disclosed apparently effective argininamide compounds for use as antithrombotic agents. The chemical structures described in these documents represent variations of side groups on the argininamide compound (U.S. Pat. No. 4,173,630; U.S. Pat. No. 4,097,591; CA 1,131,621; U.S. Pat. No. 4,096,255; U.S. Pat. No. 4,046,876; U.S. Pat. No. 4,097,472; CA 2,114,153).

Canadian patent applications 2,076,311 and 2,055,850 disclose cyclic imino derivatives that exhibit inhibitory effects on cellular aggregation.

Many of the examples cited above are convergent by maintaining at least a linear acyclic tripeptidyl motif, consisting of an arginyl unit whose basic side chain is required for interaction with a carboxylate group located at the base of the $S_1$ specificity cleft in thrombin. Two adjacent hydrophobic groups provide additional binding through favorable Van der Waals interactions within a contiguous hydrophobic cleft on the enzyme surface designated the $S_3$–$S_2$ site.

Previously, it has been demonstrated that some pyrrolo [1,2-a]pyrazine-1,4-diones are endothelin antagonists (see WO 9323404 and CA 2121724) and active as central nervous system agents (Farmaco, Ed. Sci., 1984; 39(8) :718–738). Others have demonstrated that pyrrolopyrazinediones (DE 2354056) are useful as anxiolytics and sedatives and are herbicides (U.S. Pat. No. 4,929,270).

None of the above articles disclose compounds of Formula I which are inhibitors of serine proteases.

One object of the present invention is to provide serine protease inhibitors that display inhibitory activity towards enzymes involved in the coagulation cascade and principally the target enzymes, thrombin, Factor Xa, and Factor VIIa.

A further object of the present invention is to provide serine protease inhibitors that display inhibitory activity towards the target enzyme thrombin and are provided for in a pharmacologically acceptable state.

Still a further object of the present invention is to provide for the use of these thrombin inhibitors and formulations thereof as anticoagulant and thrombin inhibitory agents.

Yet a further object of the present invention is to provide for the use of these thrombin inhibitors and formulations thereof for therapeutic treatment of various thrombotic maladies.

A further object of the present invention is a process for the synthesis of these low molecular weight thrombin inhibitors. The enzyme inhibitors of the present invention are encompassed by the structure of general Formula I.

SUMMARY OF THE INVENTION

The present invention provides for novel compounds that display thrombin inhibitory activity as reflected in Formula I.

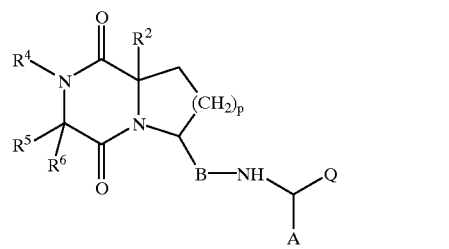

wherein:

B is either C=O or $CH_2$, $R^1$ is selected from H, Cl, Br, I, F, $NR^2R^3$, $OR_2$, $NO_2$, CN, $CF_3$, $C(=O)R^2$, $S(O)_p$, $R^2$, $CONHR^2$, $CO_2R^2$, aryl, heterocycle;

$R^2$ is selected from H, $C_{1-6}$ alkyl;

$R^3$ is selected from H, $C_{1-6}$ alkyl;

$R^4$ is selected from H, $C_{1-6}$ alkyl optionally substituted by a group selected from $R^1$ and where the alkyl chain may be interrupted by one or more heteroatoms selected from O, N, S and so that the heteroatoms are not adjacent;

$R^5$ is selected from H, $C_{1-6}$ alkyl optionally substituted by a group selected from $R^1$;

$R^6$ is selected from H, $C_{1-6}$ alkyl optionally substituted by a group selected from $R^1$;

$R^7$ is selected from H, $C_{1-6}$ alkyl, —$(CH_2)_n$-aryl;

A is selected from —$(CH_2)_3(CH_2)_n$—Y,

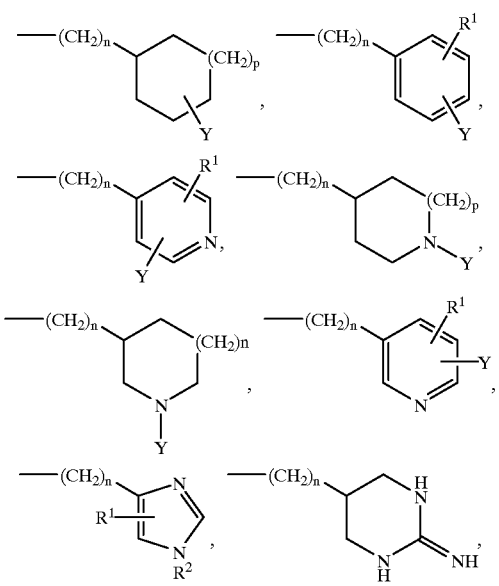

-continued

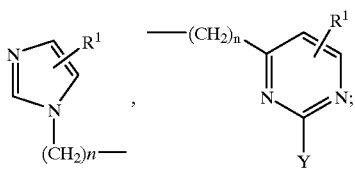

Y is selected from

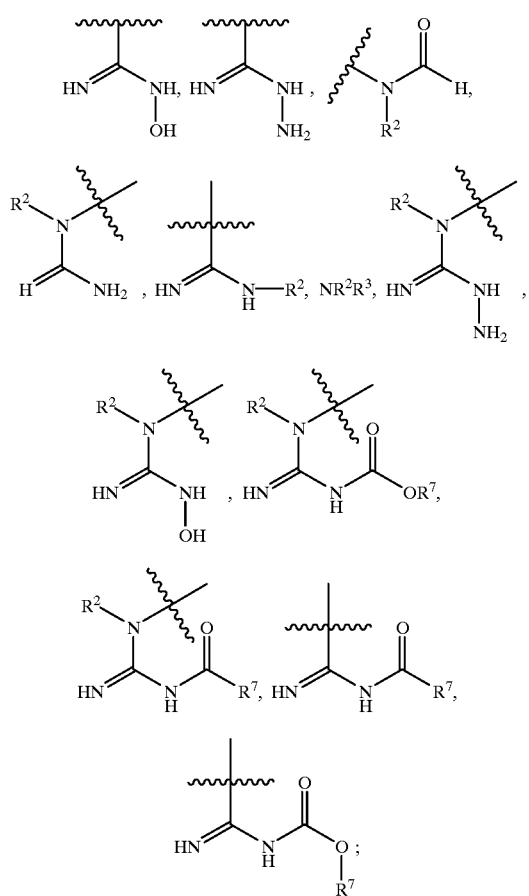

Q is selected from

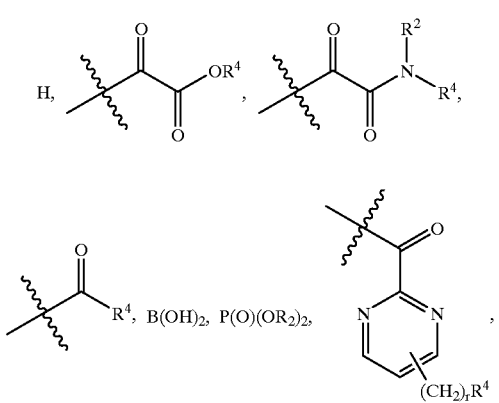

-continued

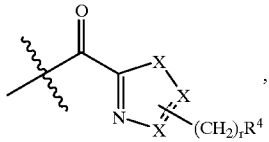

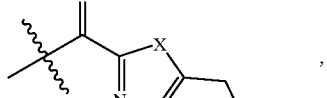

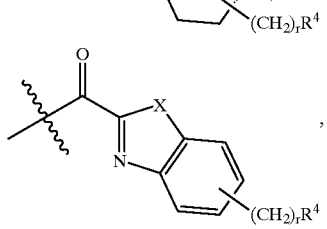

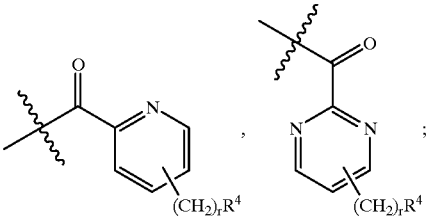

X is selected from O, $NR_4$, S;
p is selected from 0 to 2;
n is selected from 0 to 4;
r is selected from 0 to 4;

and pharmaceutically acceptable salts and solvates thereof.

Specifically preferred compounds according to this invention have the formula:

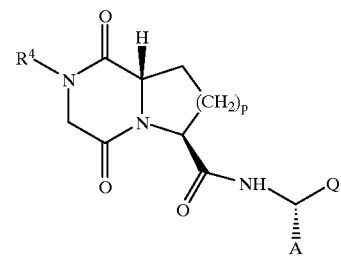

wherein:

$R^1$ is selected from H, Cl, Br, I, F, $NR^2R^3$, $OR^2$, $NO_2$, CN, $CF_3$, $COR^2$, $S(O)_p$, $R^2$, $CONHR^2$, $CO_2R^2$, aryl, heteroaryl;

$R^2$ is selected from H, $C_{1-6}$ alkyl;

$R^3$ is selected from H, $C_{1-6}$ alkyl;

$R^4$ is selected from H, $C_{1-6}$ alkyl optionally substituted by a group selected from $R^1$;

$R^7$ is $C_{1-6}$ alkyl, $-(CH_2)_n$-aryl;

A is selected from $-(CH_2)_3(CH_2)_n-Y$,

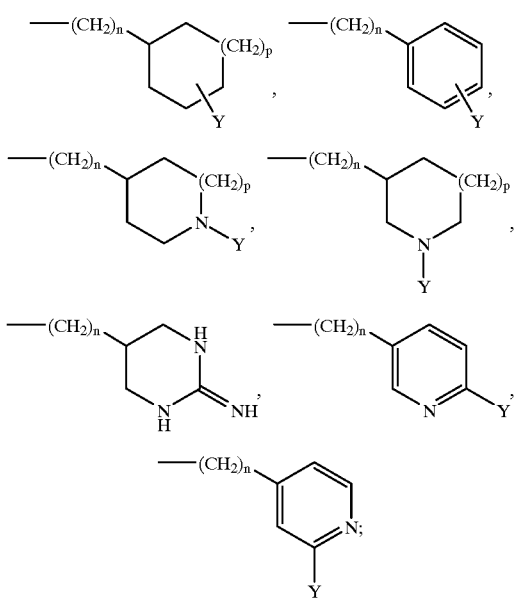
Y is selected from
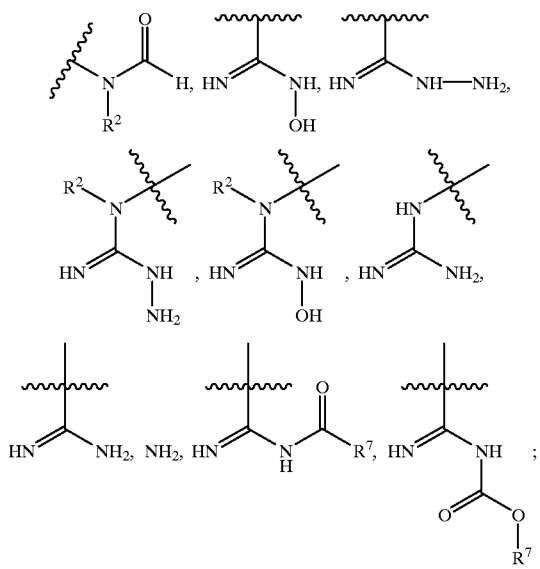
Q is selected from
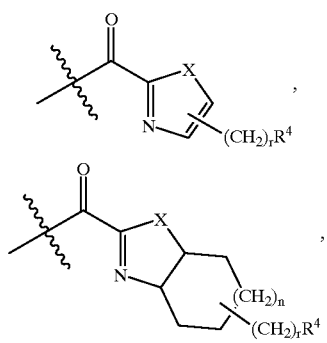
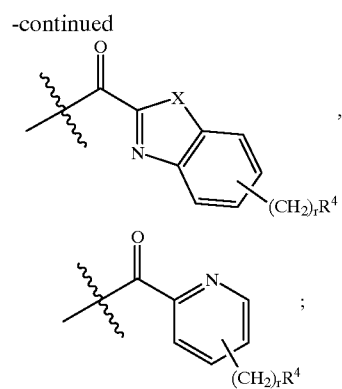
X is NR⁴, S, or O;
p is 1 or 2;
n is selected from 0 to 2, and
r is selected from 0 to 4.
Another preferred group of compounds have the formula:
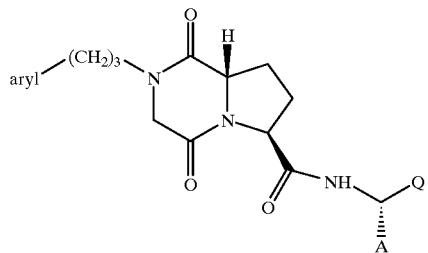
wherein:
A is selected from $-(CH_2)_3-(CH_2)_n-Y$,
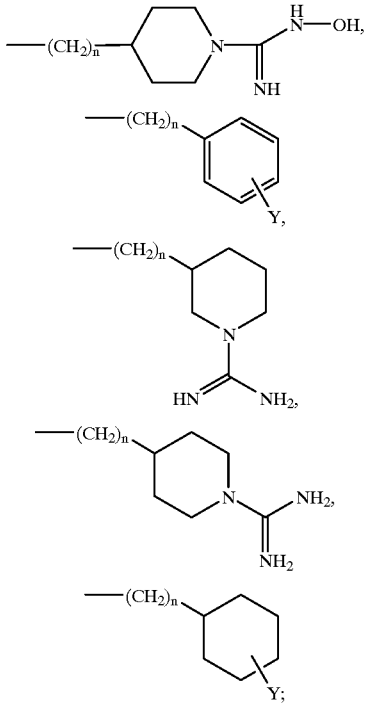

Y is selected from

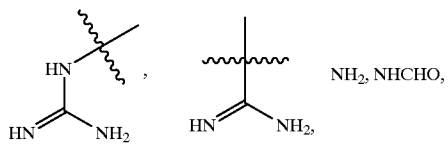

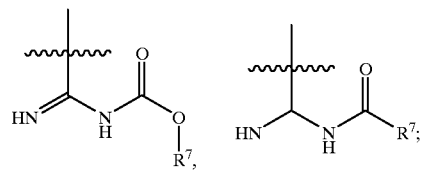

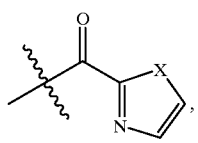

R[7] is C$_{1-6}$ alkyl, —(CH$_2$)$_n$-aryl;

Q is selected from

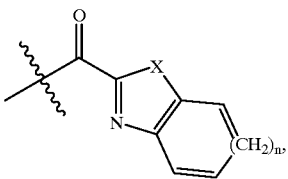

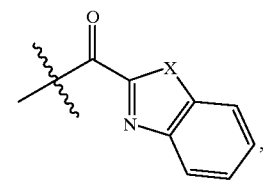

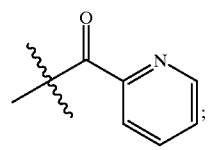

X is NMe, S, or O, and n is selected from 0 to 2.

The most preferred compounds provided by this invention are:

| Structure | Name |
|---|---|
| 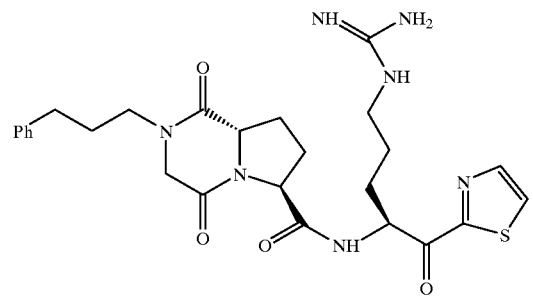 | [6S-[6α(R*),8aα]]-1,4-Dioxo-2-(3-phenyl-propyl)-octahydro-pyrrolo[1,2-a]pyrazine-6-carboxylic acid[4-guanidino-1-(thiazol-2-carbonyl)-butyl]-amide |
| 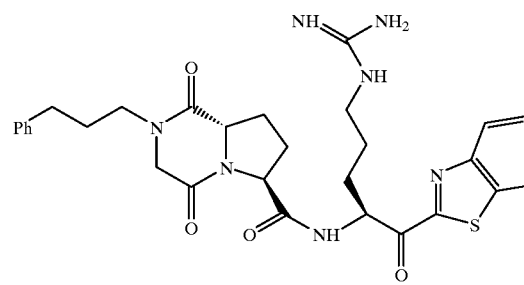 | [6S-[6α(R*),8aα]]-1,4-Dioxo-2-(3-phenyl-propyl)-octahydro-pyrrolo[1,2-a]pyrazine-6-carboxylic acid[1-(benzothiazol-2-carbonyl)-4-guanidino-butyl]-amide |

-continued

| Structure | Name |
|---|---|
| 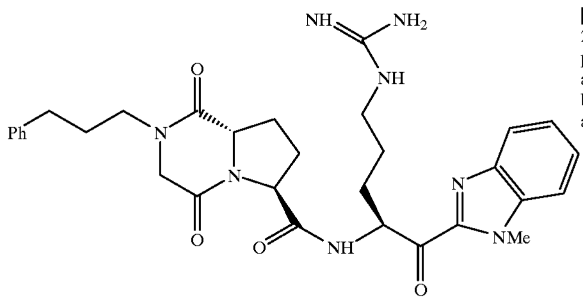 | [6S-[6α(R*),8aα]]-1,4-Dioxo-2-(3-phenyl-propyl)-octahydro-pyrrolo[1,2-a]pyrazine-6-carboxylic acid[4-guanidino-1-(1-methyl-1H-benzoimidazol-2-carbonyl)-butyl]-amide |
| 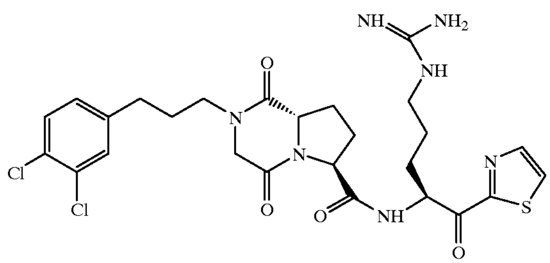 | [6S-[6α(R*),8aα]]-2-[3-(3,4-dichloro-phenyl)-propyl]-1,4-dioxo-octahydro-pyrrolo[1,2-a]pyrazine-6-carboxylic acid[4-guanidino-1-(thiazol-2-carbonyl)-butyl]-amide |
| 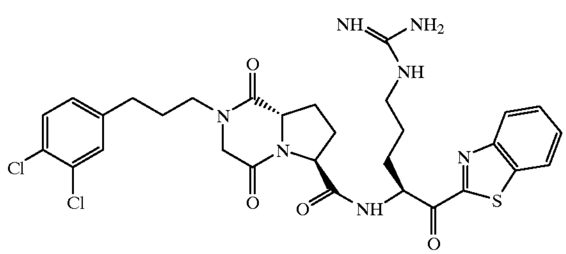 | [6S-[6α(R*),8aα]]-2-[3-(3,4-dichloro-phenyl)-propyl]-1,4-dioxo-octahydro-pyrrolo[1,2-a]pyrazine-6-carboxylic acid[1-(benzothiazol-2-carbonyl)-4-guanidino-butyl]amide |
| 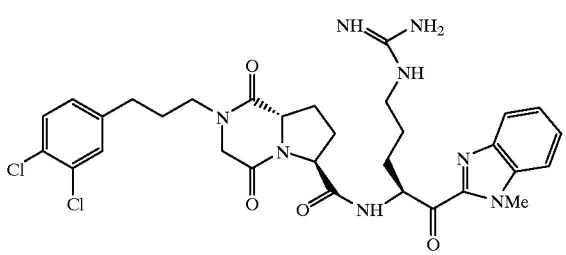 | [6S-[6α(R*),8aα]]-2-[3-(3,4-dichloro-phenyl)-propyl]-1,4-dioxo-octahydro-pyrrolo[1,2-a]pyrazine-6-carboxylic acid[4-guanidino-1-(1-methyl-1H-benzoimidazol-2-carbonyl)-butyl]-amide |
| 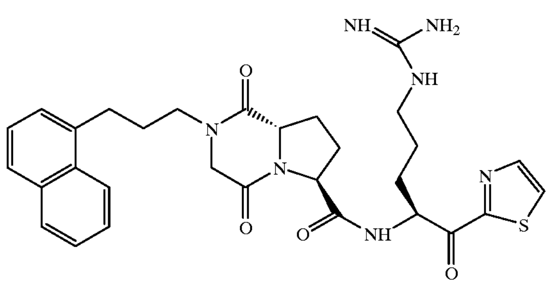 | [6S-[6α(R*),8aα]]-2-(3-Naphthalen-1-yl-propyl)-1,4-dioxo-octahydro-pyrrolo[1,2-a]pyrazine-6-carboxylic acid[4-guanidino-1-(thiazol-2-carbonyl)-butyl]-amide |

-continued

| Structure | Name |
|---|---|
| 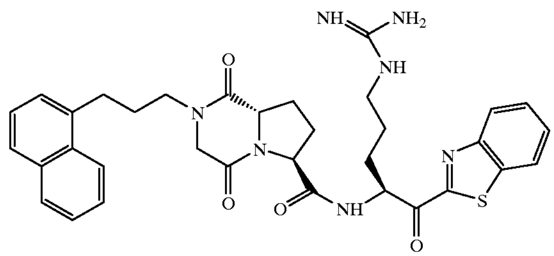 | [6S-[6α(R*),8aα]]-2-(3-Naphthalen-1-yl-propyl)-1,4-dioxo-octahydro-pyrrolo[1,2-a]pyrazine-6-carboxylic acid [1-(benzothiazol-2-carbonyl)-4-guanidino-butyl]-amide |
| 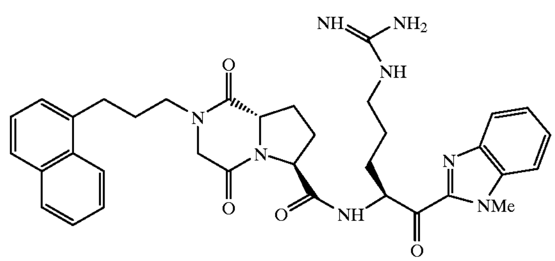 | [6S-[6α(R*),8aα]]-2-(3-Naphthalen-1-yl-propyl)-1,4-dioxo-octahydro-pyrrolo[1,2-a]pyrazine-6-carboxylic acid [4-guanidino-1-(1-methyl-1H-benzoimidazol-2-carbonyl)-butyl]-amide |
| 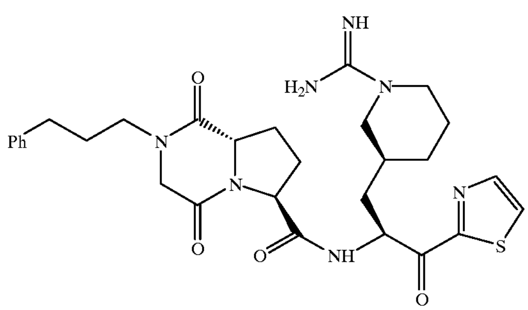 | [6S-[6α[R*(R*)],8aα]]-1,4-Dioxo-2-(3-phenyl-propyl)-octahydro-pyrrolo[1,2-a]pyrazine-6-carboxylic acid[1-(1-carbamimidoyl-piperidin-3-ylmethyl)-2-oxo-2-thiazol-2-yl-ethyl]-amide |
| 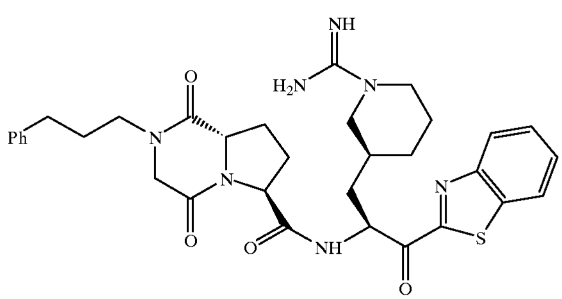 | [6S-[6α[R*(R*)],8aα]]-1,4-Dioxo-2-(3-phenyl-propyl)-octahydro-pyrrolo[1,2-a]pyrazine-6-carboxylic acid[2-benzothiazol-2-yl-1-(1-carbamimidoyl-piperidin-3-ylmethyl)-2-oxo-ethyl]-amide |
| 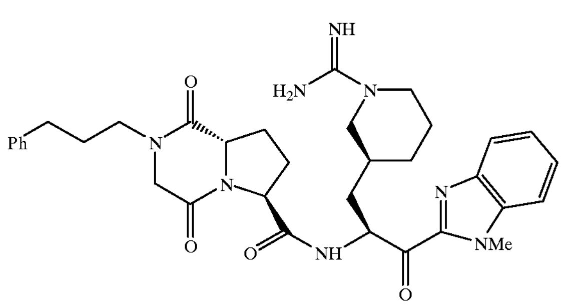 | [6S-[6α[R*(R*)],8aα]]-1,4-Dioxo-2-(3-phenyl-propyl)-octahydro-pyrrolo[1,2-a]pyrazine-6-carboxylic acid[1-(1-carbimimidoyl-piperidin-3-ylmethyl)-2-(1-methyl-1H-benzoimidazol-2-yl)-2-oxo-ethyl]-amide |

-continued

| Structure | Name |
|---|---|
| 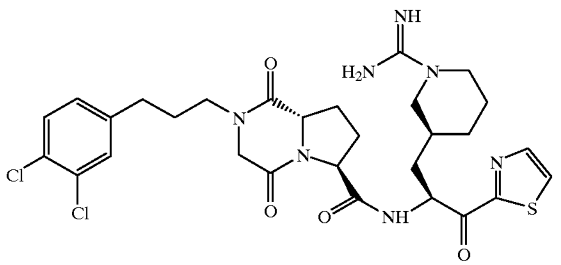 | [6S-[6α[R*(R*)],8aα]]-2-[3-(3,4-Dichloro-phenyl)-propyl]-1,4-dioxo-octahydro-pyrrolo[1,2-a]-pyrazine-6-carboxylic acid [1-(1-carbamimidoyl-piperidin-3-ylmethyl)-2-oxo-2-thiazol-2-yl-ethyl]-amide |
| 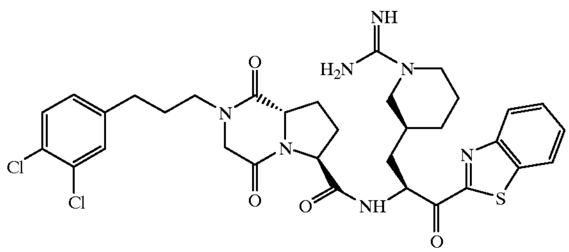 | [6S-[6α[R*(R*)],8aα]]-2-[3-(3,4-Dichloro-phenyl)-propyl]-1,4-dioxo-octahydro-pyrrolo[1,2-a]-pyrazine-6-carboxylic acid [2-benzothiazol-2-yl-1-(1-carbamimidoyl-piperidin-3-ylmethyl)-2-oxo-ethyl]-amide |
| 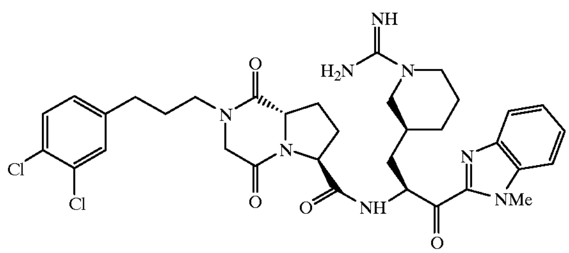 | [6S-[6α[R*(R*)],8aα]]-2-[3-(3,4-Dichloro-phenyl)-propyl]-1,4-dioxo-octahydro-pyrrolo[1,2-a]-pyrazine-6-carboxylic acid [1-(1-carbamimidoyl-piperidin-3-ylmethyl)-2-(1-methyl-1H-benzoimidazol-2-yl)-2-oxo-ethyl]-amide |
| 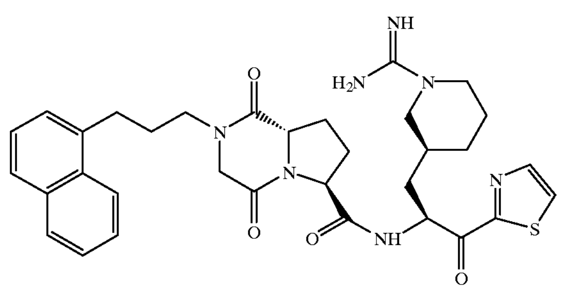 | [6S-[6α[R*(R*)],8aα]]-2-(3-Naphthalen-1-yl-propyl)-1,4-dioxo-octahydro-pyrrolo[1,2-a]-pyrazine-6-carboxylic acid [1-(1-carbimimidoyl-piperidin-3-ylmethyl)-2-oxo-2-thiazol-2-yl-ethyl]-amide |
| 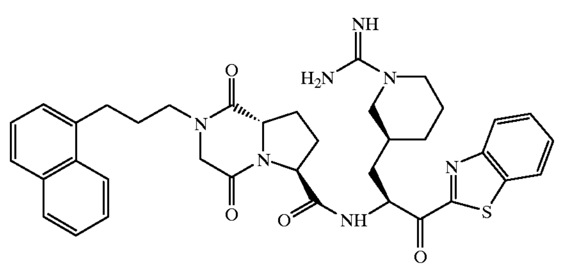 | [6S-[6α[R*(R*)],8aα]]-2-(3-Naphthalen-1-yl-propyl)-1,4-dioxo-octahydro-pyrrolo[1,2-a]-pyrazine-6-carboxylic acid [2-benzothiazol-2-yl-1-(1-carbamimidoyl-piperidin-3-ylmethyl)-2-oxo-ethyl]-amide |

-continued

| Structure | Name |
|---|---|
| | [6S-[6α[R*(R*)],8aα]]-2-(3-Naphthalen-1-yl-propyl)-1,4-dioxo-octahydro-pyrrolo[1,2-a]pyrazine-6-carboxylic acid [1-(1-carbamimidoyl-piperidin-3-ylmethyl)-2-(1-methyl-1H-benzoimidazol-2-yl)-2-oxo-ethyl]-amide |
| 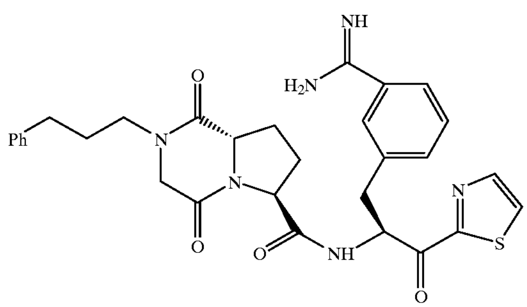 | [6S-[6α(R*),8aα]]-1,4-Dioxo-2-(3-phenyl-propyl)-octahydro-pyrrolo[1,2-a]pyrazine-6-carboxylic acid[1-(3-carbamimidoyl-benzyl)-2-oxo-2-thiazol-2-yl-ethyl]-amide |
| 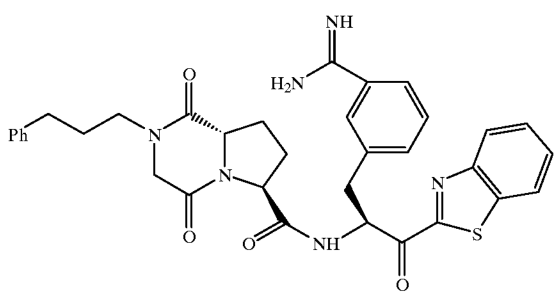 | [6S-[6α(R*),8aα]]-1,4-Dioxo-2-(3-phenyl-propyl)-octahydro-pyrrolo[1,2-a]pyrazine-6-carboxylic acid[2-benzothiazol-2-yl-1-(3-carbamimidoyl-benzyl)-2-oxo-ethyl]-amide |
| 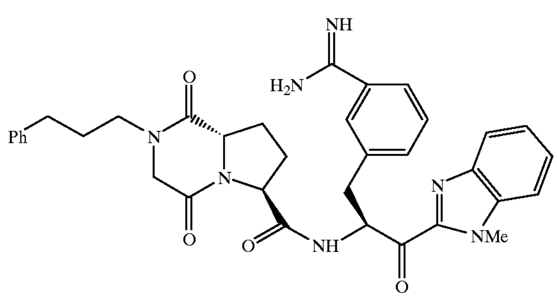 | [6S-[6α(R*),8aα]]-1,4-Dioxo-2-(3-phenyl-propyl)-octahydro-pyrrolo[1,2-a]pyrazine-6-carboxylic acid[1-(3-carbamimidoyl-benzyl)-2-(1-methyl-1H-benzoimidazol-2-yl)-2-oxo-ethyl]-amide |
| | 2-[3-(3,4-Dichloro-phenyl)-propyl]-1,4-dioxo-octahydro-pyrrolo[1,2-a]pyrazine-6-carboxylic acid [1-(3-carbamimidoyl-benzyl)-2-oxo-2-thiazol-2-yl-ethyl]-amide |

-continued

| Structure | Name |
|---|---|
| 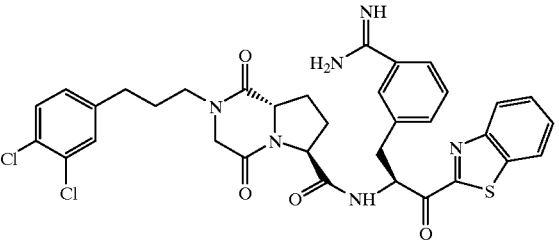 | [6S-[6α(R*),8aα]]2-[3,4-Dichloro-phenyl)-propyl]-1,4-dioxo-octahydro-pyrrolo[1,2-a]pyrazine-6-carboxylic acid[2-benzothiazol-2-yl-1-(3-carbamimidoyl-benzyl)-2-oxo-ethyl]-amide |
| 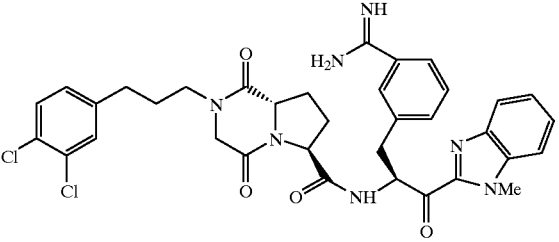 | [6S-[6α(R*),8aα]]-2-[3-(3,4-Dichloro-phenyl)-propyl]-1,4-dioxo-octahydro-pyrrolo[1,2-a]-pyrazine-6-carboxylic acid [1-(3-carbamimidoyl-benzyl)-2-(1-methyl-1H-benzoimidazol-2-yl)-2-oxo-ethyl]-amide |
| 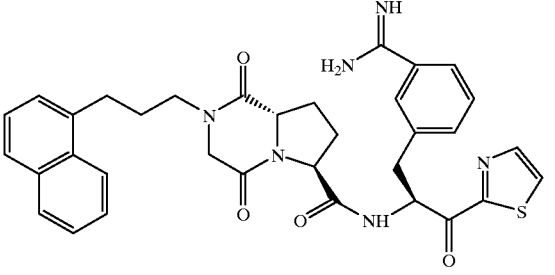 | [6S-[6α(R*),8aα]]-2-(3-Naphthalen-1-yl-propyl)-1,4-dioxo-octahydro-pyrrolo[1,2-a]pyrazine-6-carboxylic acid[1-(3-carbamimidoyl-benzyl)-2-oxo-2-thiazol-2-yl-ethyl]-amide |
| 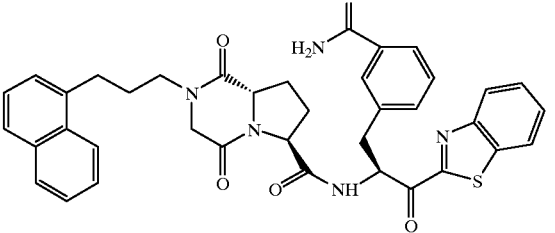 | [6S-[6α(R*),8aα]]-2-(3-Naphthalen-1-yl-propyl)-1,4-dioxo-octahydro-pyrrolo[1,2-a]pyrazine-6-carboxylic acid[2-benzothiazol-2-yl-1-(3-carbamimidoyl-benzyl)-2-oxo-ethyl]-amide |
| 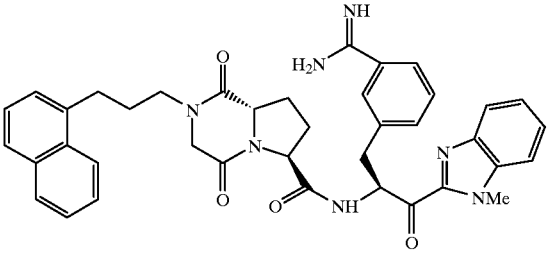 | [6S-[6α(R*),8aα]]-2-(3-Naphthalen-1-yl-propyl)-1,4-dioxo-octahydro-pyrrolo[1,2-a]pyrazine-6-carboxylic acid[1-(3-carbamimidoyl-benzyl)-2-(1-methyl-1H-benzoimidazol-2-yl)-2-oxo-ethyl]-amide |

-continued

| Structure | Name |
|---|---|
| 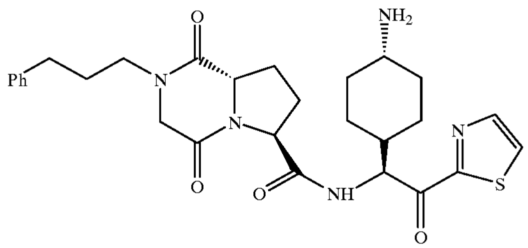 | 6S-[6α[R*(trans)],8aα]]-1,4-Dioxo-2-(3-phenyl-propyl)-octahydro-pyrrolo[1,2-a]pyrazine-6-carboxylic acid[1-(4-amino-cyclohexyl)-2-oxo-2-thiazol-2-yl-ethyl]-amide |
| 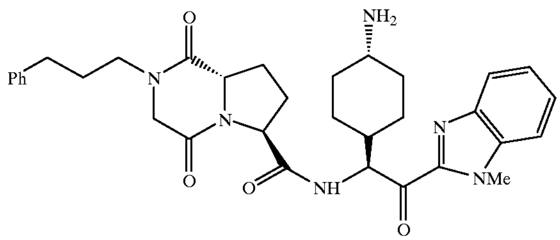 | [6S-[6αR*(trans)],8aα]]-1,4-Dioxo-(2-3-phenyl-propyl)-octahydro-pyrrolo[1,2-a]pyrazine-6-carboxylic acid[2-benzothiazol-2-yl-1-(4-amino-cyclohexyl)-2-oxo-ethyl]-amide |
| 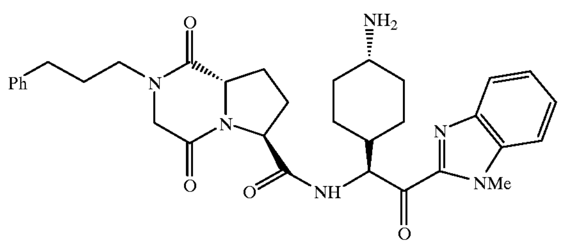 | [6S-[6αR*(trans)],8aα]]-1,4-Dioxo-(2-3-phenyl-propyl)-octahydro-pyrrolo[1,2-a]pyrazine-6-carboxylic acid[1-(4-amino-cyclohexyl)-2-(1-methyl-1H-benzoimidazol-2-yl)-2-oxo-ethyl]-amide |
| 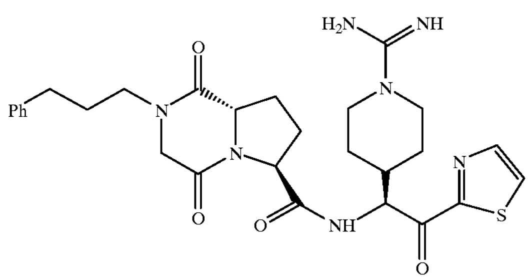 | [6S-[6α(R*),8aα]]1,4-Dioxo-2-(3-phenyl-propyl)-octahydro-pyrrolo[1,2-a]pyrazine-6-carboxylic acid[1-(1-carbamimidoyl-piperidin-4-yl)-2-oxo-2-thiazol-2-yl-ethyl]-amide |
| 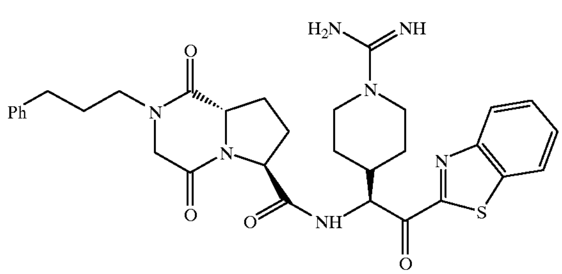 | [6S-[6α(R*),8aα]]-1,4-Dioxo-2-(3-phenyl-propyl)-octahydro-pyrrolo[1,2-a]pyrazine-6-carboxylic acid [2-benzothiazol-2-yl-1-(1-carbamimidoyl-piperidin-4-yl)-2-oxo-ethyl]-amide |

-continued

| Structure | Name |
|---|---|
| 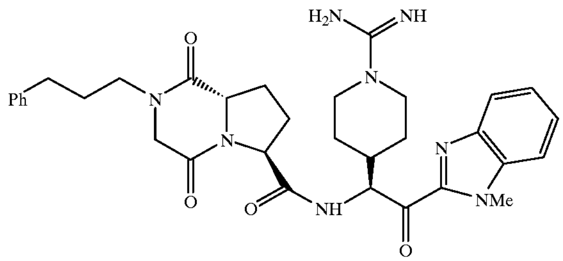 | [6S-[6α(R*),8aα]]-1,4-Dioxo-2-(3-phenyl-propyl)-octahydro-pyrrolo[1,2-a]pyrazine-6-carboxylic acid[1-(1-carbamimidoyl-piperidin-4-yl)-2-(1-methyl-1H-benzoimidazol-2-yl)-2-oxo-ethyl]-amide |
| 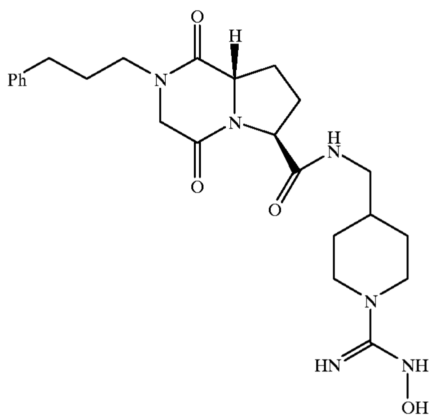 | Octahydro-N-[[1-[(hydroxyamino)iminomethyl]-4-piperidinyl]methyl]-1,4-dioxo-2-(3-phenylpropyl)pyrrolo[1,2-a]pyrazine-6-carboxamide |
| 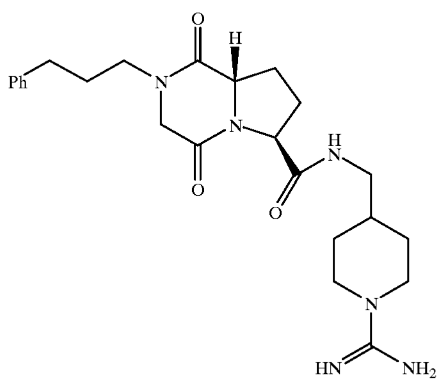 | 1,4-Dioxo-2-(3-phenyl-propyl)-octahydro-pyrrolo[1,2-a]pyrazine-6-carboxylic acid(1-carbamimidoyl-piperidin-4-ylmethyl)-amide |
| 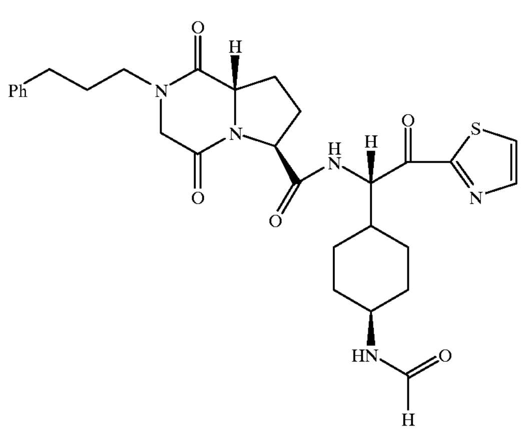 | 1,4-Dioxo-2-(3-phenyl-propyl)-octahydro-pyrrolo[1,2-a]pyrazine-6-carboxylic acid(1-(4-formylamino-cyclohexyl)-2-oxo-2-thiazol-2-yl-ethyl]-amide |

-continued

| Structure | Name |
|---|---|
| 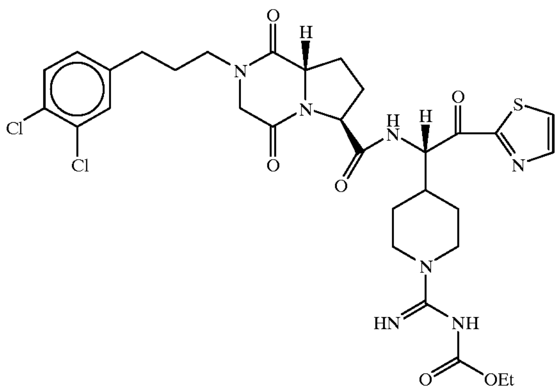 | ({4-[1-({2-[3-(3,4-Dichloro-phenyl)-propyl]-1,4-dioxo-octahydro-pyrrolo[1,2-a]pyrazine-6-carbonyl}-amino)-2-oxo-2-thiazol-2-yl-ethyl]-piperidin-1-yl}-imino-methyl)-carbamic acid ethyl ester |
| 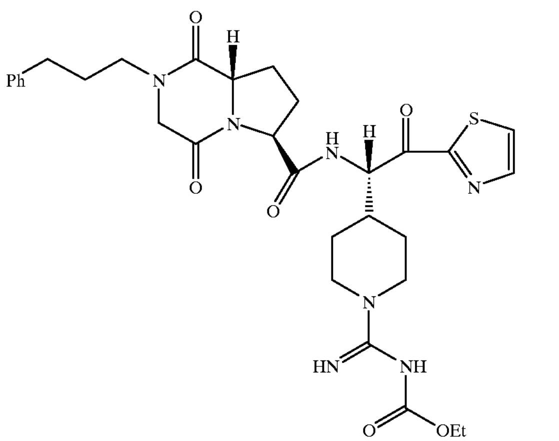 | 1,4-Dioxo-2-(3-phenyl-propyl)-octahydro-pyrrolo[1,2-a]pyrazine-6-carboxylic acid {1-[1-(imino-propionylamino-methyl)-piperidin-4-yl]-2-oxo-2-thiazol-2-yl-ethyl}-amide |

The invention also provides pharmaceutical formulations comprising a compound of Formula I together with a pharmaceutically acceptable excipient, carrier, or diluent therefor.

A further embodiment of the invention is a method for treating or preventing a thrombotic disorder in a mammal comprising administering to said mammal an antithrombotic amount of a compound of Formula I. The invention compounds are inhibitors of serine protease enzymes, and the invention further provides a method for inhibiting several proteases comprising administering a serine protease inhibiting amount of a compound of Formula I.

DETAILED DESCRIPTION OF THE INVENTION

The term "alkyl" means a straight, branched or cyclic, saturated or unsaturated carbon chain having from 1 to 6 carbon atoms. Typical alkyl groups include methyl, isobutyl, cyclopropyl, 2-methyl-pentyl, and the like.

The term "aryl" represents an unsaturated carbocyclic ring(s) of 6 to 16 carbon atoms, which is optionally substituted with OH, O(alkyl), SH, S(alkyl), $NH_2$, NH(alkyl), N(di-alkyl), halogen, acids, esters, amides, alkyl ketones, aldehydes, nitrile, fluoroalkyl, nitro, sulfone, sulfoxide, or alkyl. Typical rings include phenyl, naphthyl, phenanthryl, and anthracenyl. Preferred aryl rings are phenyl, substituted phenyl, and naphthyl. Preferred substituents on phenyl rings are halogens to afford, for example, 3,4-dichlorophenyl.

The term "heteroatom" as used herein represents oxygen, nitrogen, or sulfur (O, N, or S) as well as sulfoxyl or sulfonyl (SO or $SO_2$) unless otherwise indicated. It is understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl.

The term "heterocycle" means a saturated or unsaturated mono- or polycyclic (eg, bicyclic) ring incorporating one or more (eg, 1–4) heteroatoms selected from N, O, and S. It is understood that a heterocycle may optionally be substituted with OH, O(alkyl) SH, S(alkyl), $NH_2$, NH(alkyl), N(di-alkyl), halogen, acids, esters, amides, alkyl ketones, aldehydes, nitrile, fluoroalkyl, nitro, sulfone, sulfoxide, or $C_{1-6}$ alkyl. Examples of typical monocyclic heterocycles include, but are not limited to, pyridine, piperidine, pyrazine, piperazine, pyrimidine, imidazole, thiazole, oxazole, furan, pyran, and thiophene. Examples of typical bicyclic heterocycles include, but are not limited to, benzothiophenes, benzofurans, benzothiazoles, benzooxazoles, indole, quinoline, isoquinoline, purine, and carbazole.

All stereoisomers and tautomers are included within Formula I and are provided by this invention. Individual stereoisomers are also included, and are indicated by the wedge or hash representation. When specific isomers are drawn, they are the preferred isomers.

The invention compounds readily from pharmaceutically acceptable acid addition salts by reaction with common inorganic and organic acids. Typical acids routinely utilized include hydrochloric, hydrobromic, sulfuric, phosphoric, acetic, maleic, formic, and related acids. The compounds additionally form solvates, for example, hydrates, alcoholates, and the like.

Also provided by this invention is a method for preventing and treating a thrombotic disorder in a mammal comprising administering to such mammal an antithrombotic effective amount of a compound of Formula I. The compounds are useful as anticoagulants for the treatment and prophylaxis of thrombotic disorders such as venous and arterial thrombosis, pulmonary embolism, and ischemic events such as myocardial infarction or cerebral infarction. These compounds also have therapeutic utility for the prevention and treatment of coagulpathies associated with coronary bypass operations and restenosis following transluminal angioplasty. These compounds are useful for preventing or treating unstable angina, refractory angina, disseminated intravascular coagulation, and ocular build-up of fibrin. Since thrombin has also been demonstrated to activate a number of different cell types, these compounds are useful for the treatment or prophylaxis of septic shock and other inflammatory responses such as acute or chronic atherosclerosis. In a preferred method, the thrombotic disorder is selected from venous thrombosis, arterial thrombosis, pulmonary embolism, myocardial infarction, and cerebral infarction. The compounds also have utility in treating neoplasia/metastasis and neurodegenerative diseases such as Alzheimer's and Parkinson's disease. A further embodiment of this invention is a pharmaceutical formulation comprising a compound of Formula I admixed with a diluent, excipient, or carrier therefor.

The compounds of Formula I can be prepared by any of various methods known to those skilled in the art of organic chemistry. The following scheme illustrates one particular method of preparation:

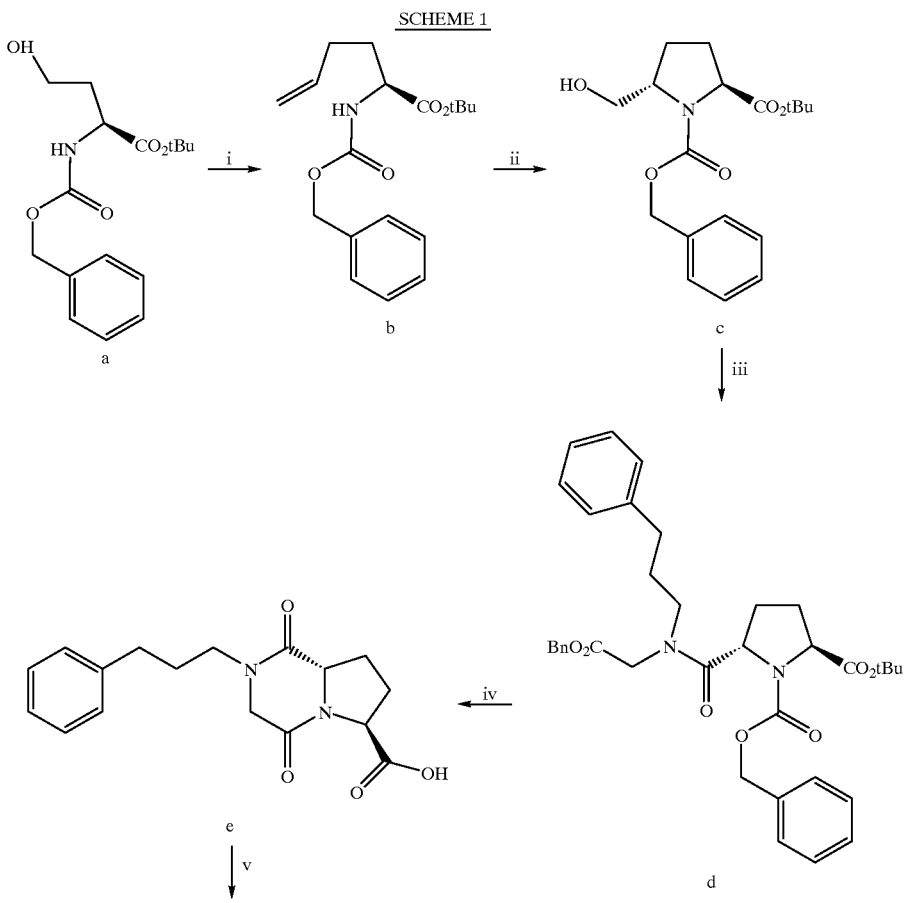

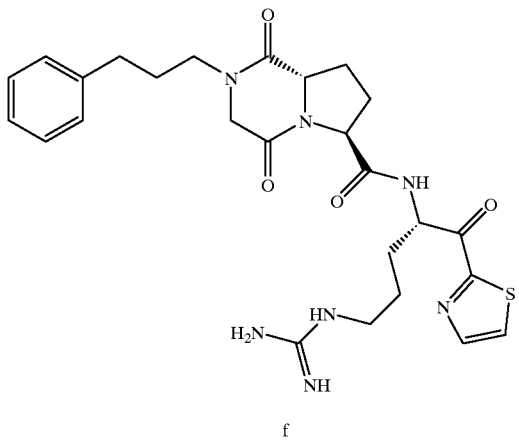

f

Step I

The alcohol is converted to the iodide via activation of the alcohol as a sulphonate ester, typically a mesylate, and then by treatment with, for example, sodium iodide in a solvent such as DMF or acetone. Alternatively, the alcohol can be converted directly to the iodide upon treatment with triphenyl phosphine and iodine. This iodide then, upon treatment with an organometallic agent such as a vinyl cuprate, affords the unsaturated addition adduct (b).

Step ii

A mercury-catalyzed cyclization process via treatment of the intermediate (b) with a mercury salt such as mercury acetate, followed by treatment with oxygen gas in the presence of sodium borohydride, affords the intermediate alcohol (c).

Step iii

Oxidation of the alcohol (c) with typical oxidizing reagents such as pyridinium dichromate (PDC), Dess-Martin periodinane, or oxalyl chloride/DMSO readily affords the intermediate aldehyde, which is further oxidized to the corresponding acid with an oxidizing reagent such as sodium chlorite. Alternatively, the alcohol (c) can be converted directly to the acid with reagents such as PDC in DMF. This acid is reacted with an amine in the presence of an activating reagent, such as benzotriazol-1-yloxy-tris (dimethylamino) phosphonium hexafluorophosphate (BOP-reagent), to form the amide intermediate (d).

Step iv

Hydrogenation of the intermediate (d) in the presence of a transition metal catalyst, such as Pd/C, and a hydrogen atmosphere results in deprotection of the aryl protecting groups and then allows treatment of the resultant product with BOP-reagent and then TFA to afford the bicyclic intermediate (e).

Step v

Compound (e) is reacted with an appropriately protected keto-heterocyclearginine derivative in the presence of an activating reagent such as BOP-reagent to form the amide (f). The guanine protecting group, typically an arylsulfonyl group, is removed by TFA, or HF treatment, to afford compounds of Formula I, as exemplified by compound (f).

Scheme 2 depicts an alternative method for preparing compounds of this invention. An aldehyde such as (1) is converted to the amino acid (4) via formation of the hydantoin with ammonium carbonate and potassium cyanide. The hydantoin is reduced, typically with hydrogen gas and a transition metal to form the saturated piperidine derivative 3. Aqueous base treatment at elevated temperatures affords the amino acid derivative 4. The amino group can be protected, with for example, by reaction with boc-anhydride, to form the derivative 5. The introduction of a heterocycle is accomplished by conversion of the acid to a N,O-dimethyl hydroxylamine and treatment with a lithiated heterocycle such as 2-thiazole lithium to form 7. Subsequent reduction with sodium borohydride, deprotection with trifluoroacetic acid and concomitant addition of trifluoroacetic anhydride forms the amide 9. The guanine derivative 10 is then prepared by treatment with bis-BOC-pyrazole and the trifluoroacetamide is then hydrolyzed with aqueous base. This amino alcohol is treated with the appropriate carboxylic acid in the presence of a coupling reagent, such as HATU, to afford the amide. Oxidation by reaction with an oxidizing agent such as Dess-Martin periodinane forms the keto thiazole which is deprotected with trifluoroacetic acid to afford the compounds of type 13. This compound may then be derivatized with ethylchloroformate to afford the compounds of type 14 wherein $R_7$ is ethyl.

SCHEME 2

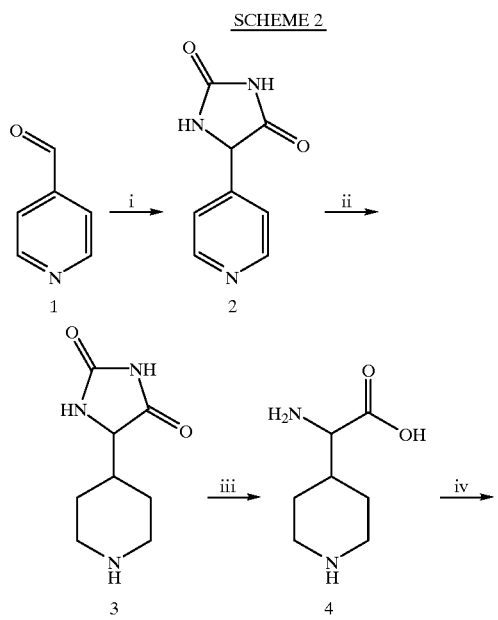

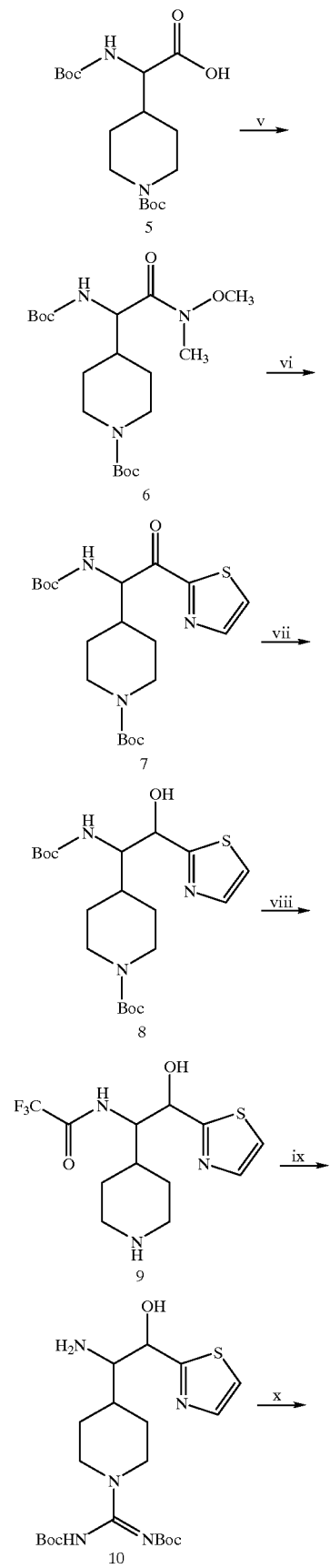

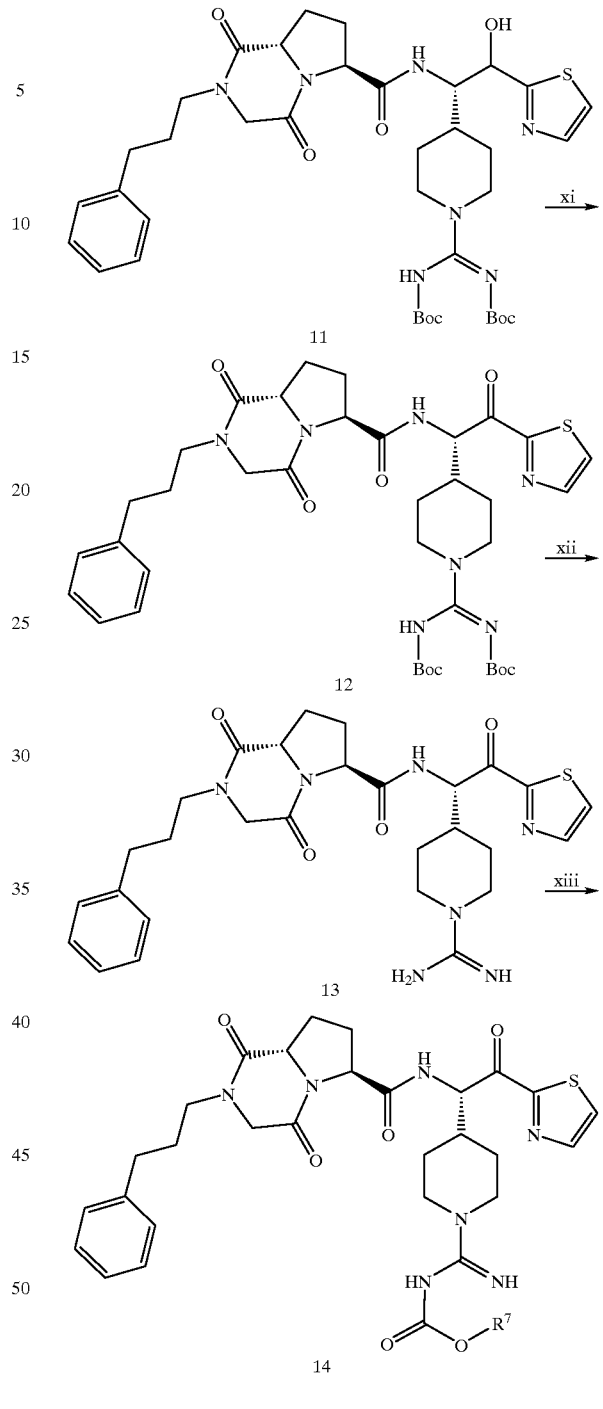

Scheme 3 depicts yet a further example of a procedure that may be used for preparing compounds of Formula I. In this scheme, the pyrrolopyrazine-1,4-dione carboxylic acid 15 is treated with the Boc protected 4-aminomethylpiperidine derivative to form 16. Treatment with acid such as trifluoroacetic acid and then addition of cyanogen bromide and base afford the N-cyano adduct 17. Addition of hydroxylamine forms adduct 18, whereas sequential treatment with hydrogen sulfide, methyliodide and hydrazine affords the adduct 19.

SCHEME 3

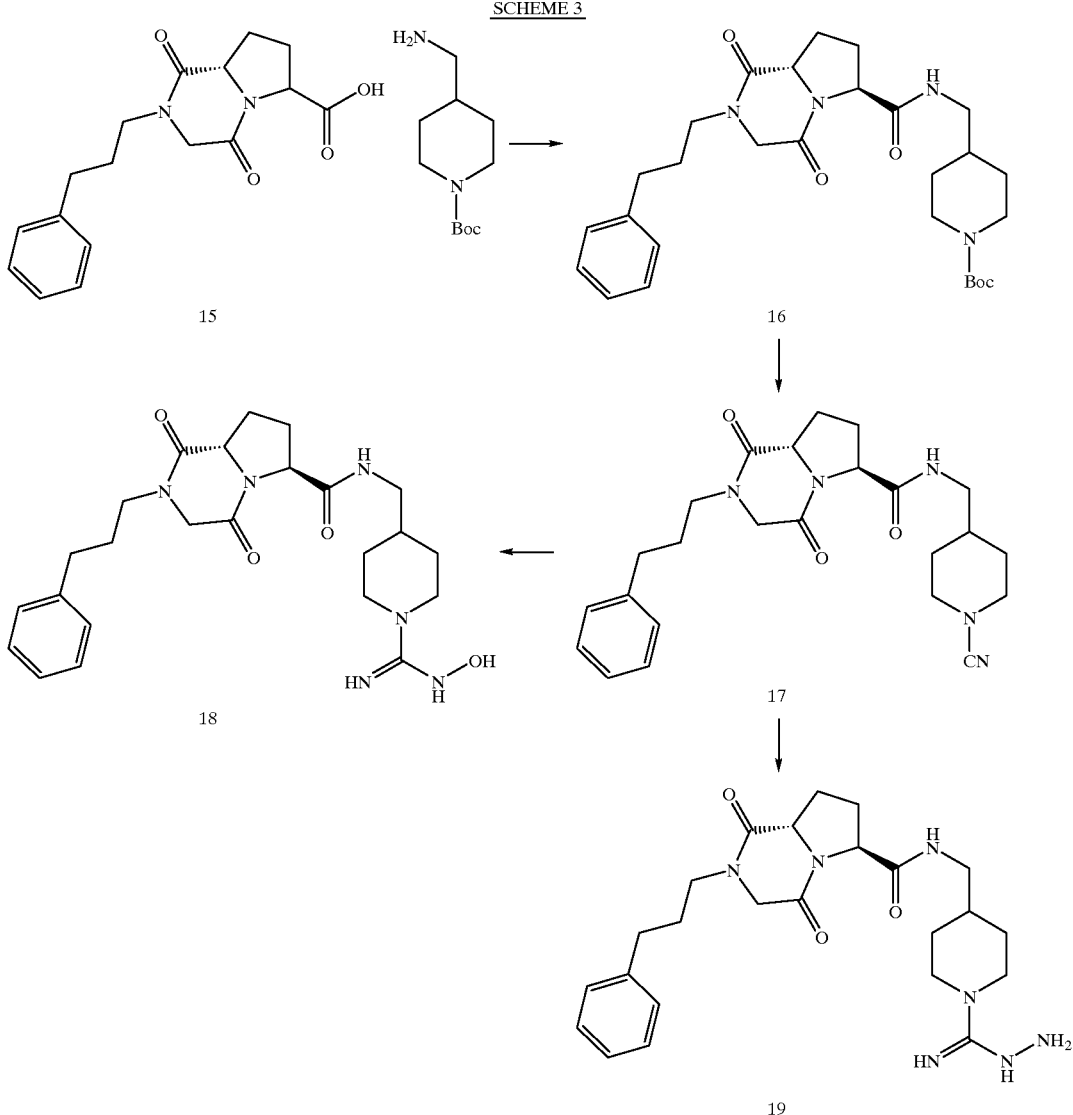

BIOLOGY

Compounds of the present invention are further characterized by their ability to inhibit the catalytic activity of thrombin, which is demonstrated in the assay as follows. Compounds of the present invention may be prepared for assay by dissolving them in buffer to give solutions ranging in concentrations from 1 to 100 μM. In an assay to determine the inhibitory dissociation constant, $K_i$, for a given compound, a chromogenic or fluorogenic substrate of thrombin is added to a solution containing a test compound and thrombin; the resulting catalytic activity of the enzyme is spectrophotometrically determined. This assay is well-known to those skilled in the art and is commonly used to determine antithrombotic activity.

The compounds of the present invention may be used as anticoagulants in vitro or ex vivo, as in the case of contact activation with foreign thrombogenic surfaces such as that found in tubing used in extracorporeal shunts. The compounds of the invention may also be used to coat the surface of such thrombogenic conduits. To this end, the compounds of the invention can be prepared as lyophilized powders, redissolved in isotonic saline or similar diluent, and added in an amount sufficient to maintain blood in an anticoagulated state.

The therapeutic agents of the present invention may be administered alone or in combination with pharmaceutically acceptable carriers. The proportion of each carrier is determined by the solubility and chemical nature of the compound, the route of administration, and standard pharmaceutical practice. For example, the compounds may be injected parenterally, this being intramuscularly, intravenously, or subcutaneously. For parenteral administration, the compound may be used in the form of sterile solutions containing other solutes, for example, sufficient saline or glucose to make the solution isotonic. The compounds may be administered orally in the form of tablets, capsules, or granules containing suitable excipients such as starch, lactose, white sugar, and the like. The compounds may also be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and/or flavoring agents. Typical formulations will contain from about 5% to 95% by weight of an invention compound.

The amount of invention compound to be utilized to prevent and treat thrombotic disorders is that amount which is effective to prevent or treat the condition without causing unacceptable side effects. Such effective amounts will be from about 0.01 mg/kg to about 500 mg/kg, preferably from about 1 mg/kg to about 100 mg/kg. Physicians will determine the precise dosage of the present therapeutic agents which will be most suitable. Dosages may vary with the mode of administration and the particular compound chosen. In addition, the dosage may vary with the particular patient under treatment.

When the composition is administered orally, a larger quantity of the active agent will typically be required to produce the same effect as caused with a smaller quantity given parenterally.

To further assist in understanding the present invention, the following nonlimiting examples of the synthesis of specific thrombin inhibitory compounds of Formula I are provided. The following examples, of course, should not be construed as specifically limiting the present invention, variations presently known, or later developed which would be within the purview of one skilled in the art are considered to fall within the scope of the present invention as described herein. The preferred compounds as of the present invention are synthesized using conventional preparative steps and recovery methods known to those skilled in the art of organic and bio-organic synthesis, while providing a new and unique combination for the overall synthesis of each compound. Preferred synthetic routes for intermediates involved in the synthesis as well as the resulting antithrombotic compounds of the present invention follow.

EXAMPLE 1

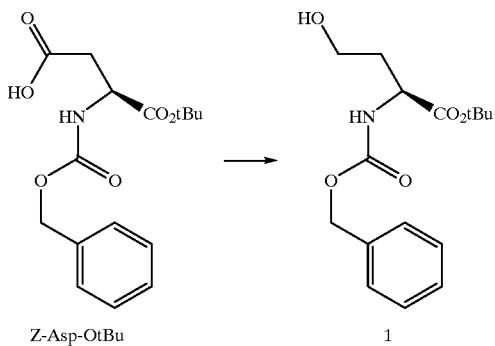

Z-Asp-OtBu        1

To a solution of the protected Z-Asp-OtBu•DCHA (15 g) in 297 mL of dry tetrahydrofuran (THF), at −10° C., under $N_2$, was added N-methylmorpholine (0.654 mL) and isopropyl chloroformate (1.0 M/toluene:33 mL). The solution was stirred at −10° C. for 60 minutes. In another flask, $NaBH_4$ (2.25 g) was suspended in a dry 5:1 mixture of THF/MeOH (297 mL), at −78° C., under $N_2$. This suspension was stirred at −78° C. for 30 minutes. The mixed anhydride solution was then added to the $NaBH_4$ suspension dropwise via cannula, and the final solution was stirred at −78° C. for 3 hours. Acetic acid (17 mL) was then added, and the solution was warmed to room temperature (30 minutes). The solvents were evaporated, the residue taken up in EtOAc, and washed with sat.aq. $NaHCO_3$ (2×) and brine. The organic layer was dried over $MgSO_4$, the solids were filtered, and the solvent evaporated to give 9.1 g of the alcohol (1) as a clear oil.

$^1$H NMR (CDCl$_3$, 400 MHz): 7.40–7.31 (m, 5H, ArH), 5.63 (d, 1H, J=7.3, NH), 5.13 (AB system, 2H, J=12.2, CH$_2$Ph), 4.43 (m, 1H, H-2), 3.69 (m, 2H, H-4), 2.17 (m, 1H, H-3), 1.63 (m, 1H, H-3), 1.48 (s, 9H, t-Bu).

EXAMPLE 2

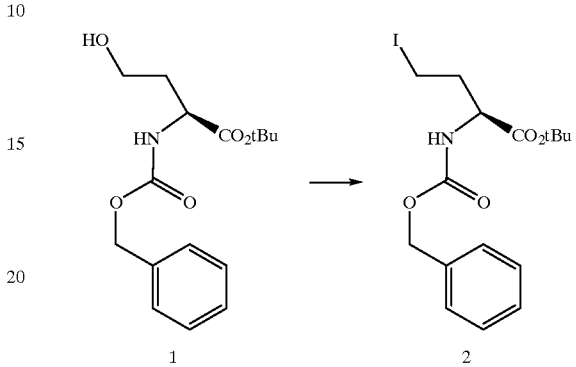

1        2

To a solution of the alcohol (1) (1.53 g, 4.95 mmol) in a 1:1 mixture of CH$_3$CN/Et$_2$O (50 mL), at −10° C., under $N_2$ were added successively imidazole (607 mg, 1.8 eq) and Ph$_3$P (2.21 g, 1.7 eq). Iodine (2.14 g, 1.7 eq) was then added in small portions over a period of 15 minutes. After the addition was completed, a white precipitate formed, and the solution was brown. It was stirred at −10° C. for 45 minutes. It was then poured in Et$_2$O, and the organic phase was washed with sat.aq. Na$_2$SO$_3$, sat.aq. CuSO$_4$, H$_2$O, and dried over MgSO$_4$. The solids were filtered and the solvent evaporated to give a yellow oil that was purified by flash chromatography (silica gel, 5% to 20% EtOAc/Hex). The iodide (2) was obtained in 83% yield (1.71 g) as a clear oil.

$^1$H NMR (CDCl$_3$, 400 MHz): 7.41–7.31 (m, 5H, ArH), 5.35 (bd, 1H, J=7.3, NH), 5.13 (s, 2H, CH$_2$Ph), 4.30 (m, 1H, H-2), 3.22–3.12 (m, 2H, H-4), 2.42 (m, 1H, H-3), 2.20 (m, 1H, H-3), 1.48 (s, 9H, t-Bu).

EXAMPLE 3

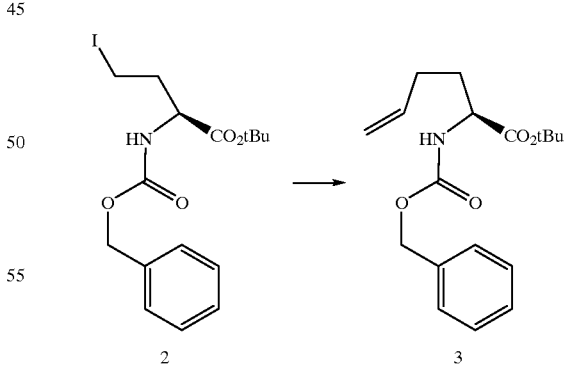

2        3

To a suspension of CuI (2.27 g, 5 eq) in dry THF (20 mL), at −78° C., under $N_2$ was added slowly a 1.0 M solution in THF of vinyl magnesium bromide (23.4 mL, 9.8 eq). The solution was then warmed up to −10° C. for 30 minutes (it turned then black) and cooled back to −78° C. A solution of the iodide (2) (1.00 g, 2.39 mmol) in dry THF (3.5 mL) was then added slowly to the cuprate solution. The reaction mixture was stirred at −78° C. for 2.5 hours. Sat.aq. NH₄Cl (50 mL) was added, and the mixture was brought back to room temperature with vigorous stirring. It was then poured in Et₂O and stirred for 5 minutes. The dark suspension was filtered through a centered funnel, and the phases were separated. The aqueous phase was extracted with Et₂O (2×), and the combined organic extracts were dried over MgSO₄. The solids were filtered, the solvents evaporated, and the crude oil purified by flash chromatography (silica gel, 5% AcOEt/Hex) to give 0.51 g (67%) of the pure alkene (3).

¹H NMR (CDCl₃, 400 MHz): 7.37–7.31 (m, 5H, ArH), 5.80 (m, 1H, H-5), 5.33 (d, 1H, J=7.8, NH), 5.12 (s, 2H, CH₂Ph), 5.05 (d, 1H, J=17.2, H-6), 5.01 (d, 1H, J=10.4, H-6), 4.30 (q, 1H, J=7.4, H-2), 2.16–2.08 (m, 2H, H-4), 1.92 (m, 1H, H-3), 1.74 (m, 1H, H-3), 1.48 (s, 9H, t-Bu).

EXAMPLE 4

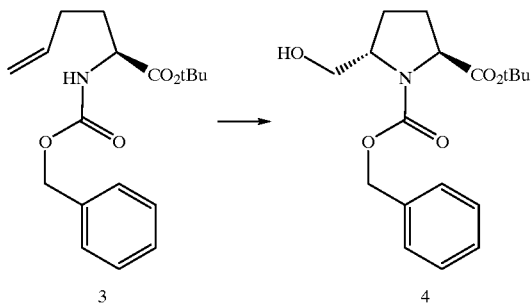

3                                    4

To a solution of the alkene (3)(50 mg, 0.157 mmol) in dry THF (3.1 mL), at r.t., under N₂, was added mercuric acetate (75 mg, 1.5 eq). The solution was stirred at room temperature for 18 hours after which it was cooled down to 0° C. Sat.aq. NaHCO₃ (2 mL) was then added, and the mixture was stirred at 0° C. for 30 minutes. KBr (0.11 g, 6 eq) was added, and the mixture was stirred at room temperature for 2 hours. It was then poured in H₂O/Et₂O, and the phases were separated. The aqueous phase was extracted with Et₂O (2×), and the combined organic extracts were dried over MgSO₄. The solids were filtered and the solvents evaporated. Oxygen (O₂) was bubbled into a suspension of NaBH₄ (3.3 mg, 0.55 eq) in dry DMF (0.4 mL) for 1 hour, and to this was added dropwise (syringe pump, 3 mL/minute) a solution of the organomercurial bromide in DMF (3.1 mL) with continuous introduction of O₂. The bubbling was continued for 1 hour and Et₂O (5 mL) was added. The gray suspension was filtered through Celite, and the filtrate was evaporated. The residue was chromatographed (silica gel, 6:4 Hex/EtOAc) to give the pyrrolidinyl (4) (30 mg, 57%) as a clear oil.

¹H NMR (CDCl₃, 400 MHz): 7.37–7.28 (m, 5H, ArH), 5.22–5.09 (m, 2H, CH₂Ph), 4.30 (dd, 1H, J=1.4, 8.3, H-2), 4.24 (m, 1H, H-5), 3.70–3.57 (m, 3H, CH₂—OH), 2.25 (m, 1H), 2.13 (m, 1H), 1.92 (m, 1H), 1.70 (m, 1H), 1.34 (s, 9H, t-Bu).

EXAMPLE 5

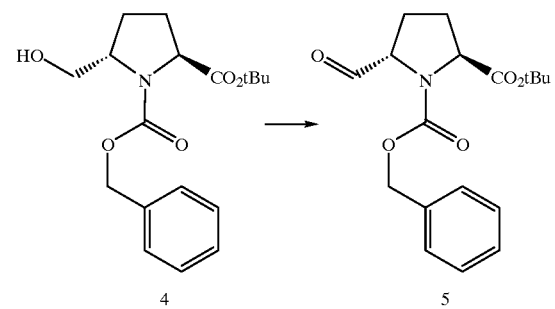

4                                    5

To a solution of the alcohol (4) (50 mg, 0.149 mmol) and Et₃N (62 mL, 3 eq) in dry CH₂Cl₂ (0.8 mL) is added slowly, under N₂, at 0° C., a solution of SO₃—Pyridine complex (71 mg, 3 eq) in dry DMSO. The solution was stirred at 0° C. for 30 minutes and 10% citric acid (2 mL) is added. The pH is brought to 4, and the aqueous phase is extracted with Et₂O (3×). The combined organic extracts were dried over MgSO₄. The solids were filtered and the solvents evaporated to give a crude oil which was purified by flash chromatography (silica gel, 7:3 Hex/EtOAc). The pure aldehyde (5) was obtained as a clear oil (45 mg, 90%).

¹H NMR (CDCl₃, 400 MHz): d 9.68–9.56 (ds, 1H, CHO), 7.36–7.29 (m, 5H, ArH), 5.23–5.11 (m, 2H, CH₂Ph), 4.57–4.39 (m, 2H, H-2, H-5), 2.30–1.97 (m, 4H, H-3, H-4), 1.47+1.36 (2s, 9H, t-Bu).

EXAMPLE 6

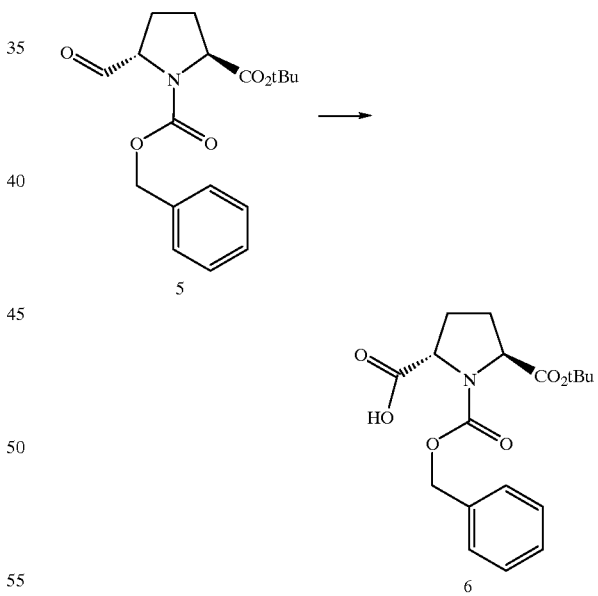

To a solution of the aldehyde (5) (0.130 g) in methanol (2 mL) and acetonitrile (2 mL) was added potassium dihydrogen phosphate (13 mg), sodium chlorite (88 mg), and then hydrogen peroxide (50 μL). The mixture was stirred for 4 hours and then acidified with 1N HCl and extracted with ethyl acetate (2×50 mL). The organic extract was washed with brine (10 mL) and then dried over MgSO₄. Evaporation in vacuo afforded the required product evident as rotational isomers (6) (0.130 g). HPLC 17.23 minutes (98%) MeCN/H₂O (0.1 TFA) 76% H₂O to 24% H₂O in MeCN gradient.

¹H NMR (CDCl₃, 300 MHz): 7.37–7.28 (m, 5H, ArH), 5.26–5.06 (m, 2H, CH₂Ph), 4.62–4.38 (m, 2H, H-2, H-5), 2.35–1.97 (m, 4H, H-3, H-4), 1.45+1.34 (2s, 9H, t-Bu).

EXAMPLE 7

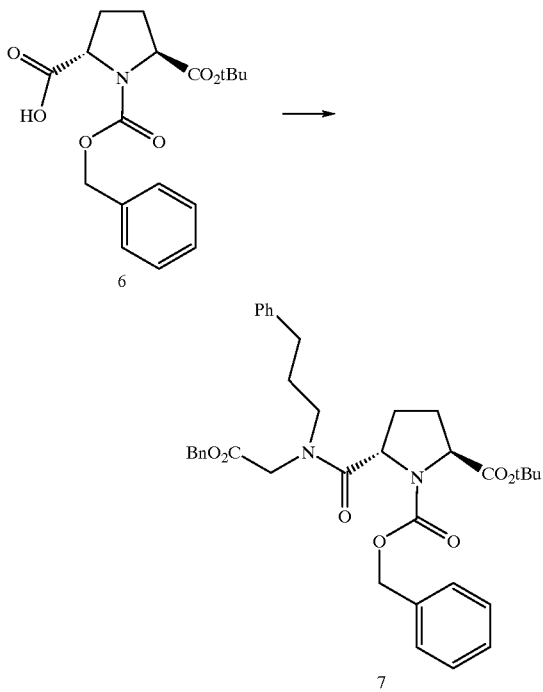

To a solution of the acid (6) in DMF (2 mL) was added diisopropylethylamine (0.130 mL), BOP-reagent (0.250 g), and then glycine, N-(3-phenylpropyl)-phenylmethyl ester (0.130 g, 1.23 eq). The mixture was stirred for 24 hours, diluted with ethyl acetate (50 mL), and washed with 1N HCl (20 mL) and then brine (20 mL). After drying over MgSO₄, the product was isolated by chromatography, eluant 50 ethyl acetate 50 hexane, to afford (7) (0.211 g, 92%). MS 614.

EXAMPLE 8

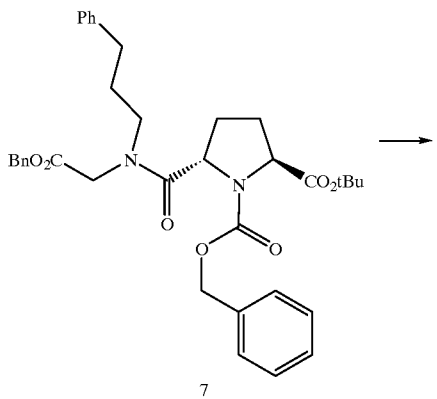

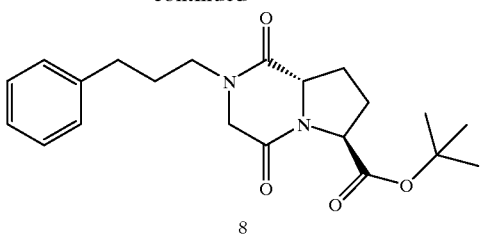

To a solution of (7) (0.210 g) in methanol (10 mL) was added palladium on carbon 10% (50 mg) and then a hydrogen balloon was attached. After 1.5 hours, the mixture was filtered and the filtrate evaporated in vacuo. The product was dissolved in DMF (3 mL) and treated with BOP-reagent (0.225 g). After stirring for 16 hours, the mixture was diluted with ethyl acetate (50 mL), washed with 1N HCl and brine (50 mL), dried over MgSO₄, filtered, and evaporated in vacuo. Purification by eluting through silica gel with ethyl acetate affords the required product (8) (0.119 g).

¹H NMR (CDCl₃, 300 MHz): 7.47–7.17 (m, 5H, ArH), 4.45 (t, J=7.9 Hz, 1H, H-2), 4.26 (t, J=7.5 Hz, 1H, H-5), 4.15 (dd, J=16.6, 1.5 Hz, 1H, NCH₂, C=O), 3.76 (d, J=16.6 Hz, 1H, NCH₂, C=O), 3.55 (m, 1H, NCH₂), 3.40 (m, 1H, NCH₂), 2.64 (t, J=7.8 Hz, 2H, PhCH₂) 2.38 (m, 2H, H-3), 2.15 (m, 2H, H-4), 1.95 (m, 2H, PhCH₂CH₂), 1.47 (s, 9H).

EXAMPLE 9

To a solution of (8) (0.120 g, 0.323 mmol) in methylene chloride (2 mL) was added trifluoroacetic acid (2 mL). The mixture was stirred at room temperature for 3 hours and then evaporated in vacuo to afford (9) (0.100 g).

¹H NMR (CDCl₃, 300 MHz): 7.31–7.16 (m, 5H, ArH), 4.57 (t, J=7.8 Hz, 1H, H-2), 4.31 (t, J=7.3 Hz, 1H, H-5), 4.19 (d, J=17.3 Hz, 1H, NCH₂, C=O), 3.94 (d, J=16.6 Hz, 1H, NCH₂, C=O), 3.50 (m, 2H, NCH₂), 2.66 (t, J=7.3 Hz, 2H, PhCH₂), 2.46 (m, 2H, H-3), 2.10 (m, 2H, H-4), 1.95 (m, 2H, PhCH₂CH₂).

EXAMPLE 10

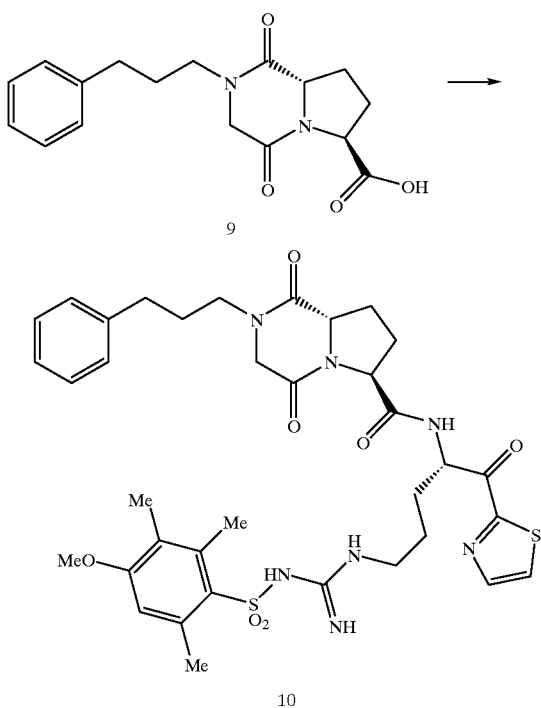

To a solution of (9) (0.100 g) in DMF (2 mL) was added (14) (S)-N-[[[4-amino-5-oxo-5-thiazol-2-yl-pentyl]amino] aminomethyl]-4-methoxy-2,3,6-trimethyl-benzenesulfonamide, HCl (0.204 g) and BOP-reagent (0.172 g), and DIEA (0.22 mL). Stirred at room temperature for 2.5 hours, diluted with ethyl acetate (50 mL), washed with 1N HCl (50 mL) and brine (50 mL), and then dried over $MgSO_4$. Chromatography, eluant 95% ethyl acetate 5% methanol, on silica gel afforded the required compound (10) (0.165 g).

EXAMPLE 11

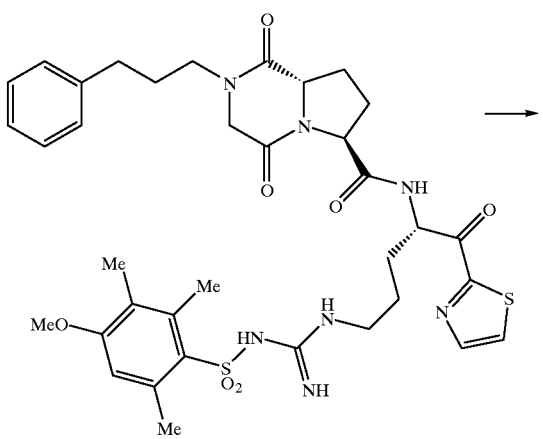

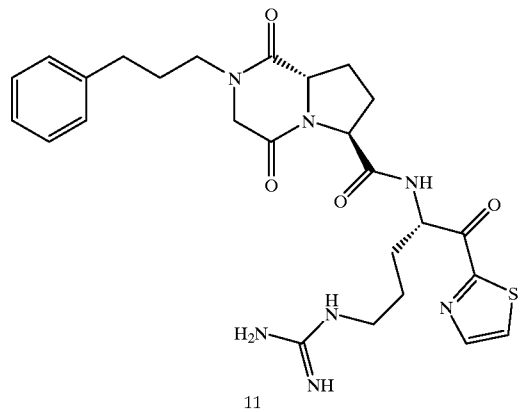

[6S-[6α(R*),8aα]]-1,4-Dioxo-2-(3-phenyl-propyl)-octahydropyrrolo[1,2-a]pyrazine-6-carboxylic acid [4-guanidino-1-(thiazol-2-carbonyl)-butyl]-amide To a mixture of (10) (0.165 g) and thioanisole (0.2 mL) was added TFA (2 mL) and the mixture stirred for 2 hours. The mixture was evaporated and purified by reverse phase HPLC, eluting with 80% acetonitrile, 20% water containing 0.1% TFA. The appropriate fractions were combined and lyophilized to afford the required compound (11) (0.095 g).

HPLC 9.46 minutes (95%) $MeCN/H_2O$ (0.1 TFA) 76% $H_2O$ to 24% $H_2O$ gradient. MS (ES) 540.

$^1$H NMR (DMSO, 300 MHz): 8.65 (d, J=7.1 Hz, 1H), 8.26 (d, J=3.0 Hz, 1H), 8.18 (d, J=3.0 Hz, 1H), 7.49 (m, 1H), 7.28–7.02 (m, 5H), 5.36 (m, 1H), 4.45 (t, J=7.3 Hz, 1H), 4.24 (m, 2H), 3.71 (m), 3.44 (m, 1H), 3.27 (m, 1H), 3.12 (m, 1H), 2.52 (t, J=6.9 Hz, 2H), 2.15 (m, 2H), 1.95 (m, 2H, H-4), 1.80–1.5 (m, 4H).

EXAMPLE 12

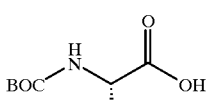

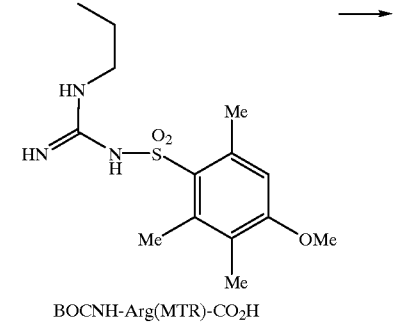

BOCNH-Arg(MTR)-$CO_2$H

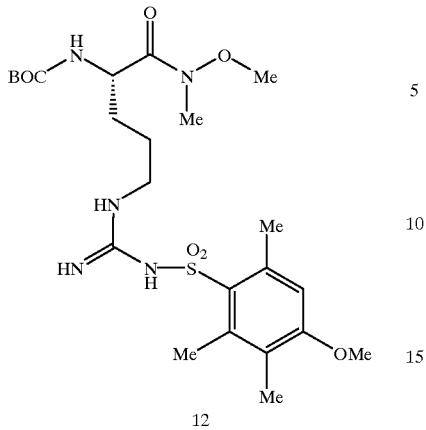

12

1,1-Dimethylethyl (S)-[4-[[imino[[(4-methoxy-2,3,
6-trimethylphenyl)sulfonyl]amino]methyl]amino]-1-
[(methoxymethylamino)carbonyl]butyl]carbamate To BocNH-Arg(MTR)-CO₂H (6.61 g, 13.6 mmol) in dichloromethane (33 mL) at 0° C. was added N-methyl morpholine (1.65 mL, 15.0 mmol) then isobutyl chloroformate (1.95 mL, 15.0 mmol). Stirred at 0° C. for 30 minutes. Added N,O-dimethyl amine HCl (1.5 g, 15.4 mmol) and N-methyl morpholine (1.65 mL, 15.0 mmol). Stirred at 0° C. for 45 minutes. Diluted with ethyl acetate (150 mL), washed with 1N HCl (2×80 mL), brine (80 mL), dried with sodium sulfate, filtered, removed solvent in vacuo, and purified with silica gel column eluted with 80% ethyl acetate in hexane to 100% ethyl acetate. Isolated 4.85 g (67.5%) of product (12) as a white foam.

¹H NMR (CDCl₃, 300 MHz): 6.52 (1H, s), 6.19 (2H, bs), 5.50 (1H, d, J=9.0 Hz), 4.63 (1H, bs), 3.82 (3H, s), 3.72 (3H, s), 3.30 (1H, bs), 3.18 (3H, s), 3.15 (3H, s), 2.69 (3H, s), 2.61 (3H, s), 2.12 (3H, s), 1.50–1.75 (4H, m), 1.41 (9H, s).

CI MS M+1=530, M+C₂H₅=558.

EXAMPLE 13

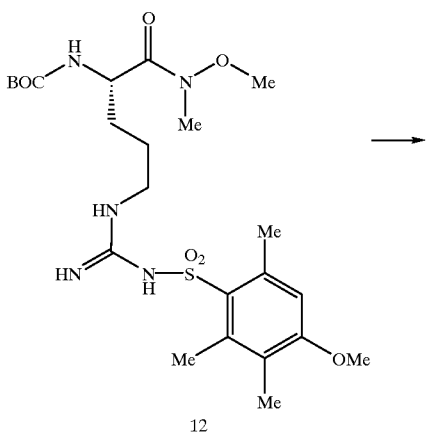

12

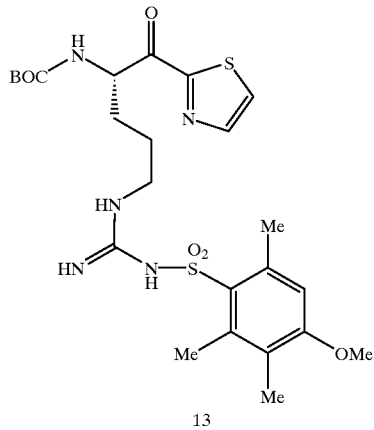

13

1,1-Dimethylethyl (S)-[4-[[imino[[(4-methoxy-2,3,
6-trimethylphenyl)sulfonyl]amino]methyl]amino]-1-
[(2-thiazolyl)carbonyl]butyl]carbamate To thiazole (1.95 mL, 27.5 mmol) and TMEDA (3.8 mL, 25.2 mmol, distilled from sodium) in THF (65 mL, freshly distilled from potassium) at −78° C. was added nBuLi in hexane (13.7 mL, 24.7 mmol, 1.8 M) at a rate that raised the internal temperature to −50° C. Placed reaction flask in dry ice/acetonitrile bath to give an internal temperature of −41° C. Stirred for 25 minutes, cooled to −78° C. Added (12) (3.18 g, 6.0 mmol) in THF (33 mL) and stirred for 45 minutes. Poured reaction over a saturated ammonium chloride solution (200 mL, aqueous) and shook vigorously. Extracted with ethyl acetate (2 ×200 mL). Combined organic phases and washed with brine (150 mL), dried with sodium sulfate, filtered, removed solvent in vacuo, purified with silica gel column eluted with 70% ethyl acetate in hexane to 100% ethyl acetate. Isolated 3.1 g (93%) of product (13) as a white foam.

¹H NMR (CDCl₃, 300 MHz): 8.06 (1H, d, J=3.00 Hz), 7.73 (1H, d, J=3.00 Hz), 6.52 (1H, s), 6.19 (2H, bs), 5.63 (1H, d, J=8.65 Hz), 5.38–5.52 (1H, m), 3.83 (3H, s), 3.50 (3H, bs), 3.19–3.31 (1H, m), 2.68 (3H, s), 2.60 (3H, s), 2.12 (3H, s), 1.50–1.75 (4H, m), 1.42 (9H, s).

CI MS M+1=554, M+C₂H₅=582.

EXAMPLE 14

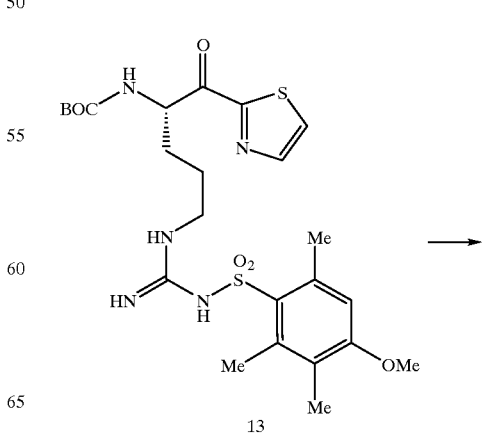

13

*-continued*

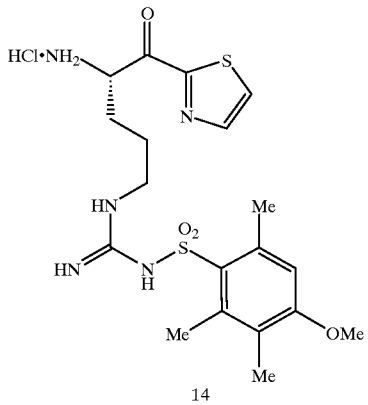

14

(S)-N-[[[4-Amino-5-oxo-5-(2-thiazolyl)pentyl]amino]iminomethyl]-4-methoxy-2,3,6-trimethyl-benzenesulfonamide To (13) (3.0 g, 5.4 mmol) in dioxane (9 mL) was added ethyl methyl sulfide (2.3 mL, 25.4 mmol) then 4M HCl in dioxane (20 mL). Stirred at room temperature for 40 minutes. A yellow, gummy precipitate formed. Decanted the supernatant. Added ethyl acetate (40 mL) and stirred the gummy precipitate to change it to a fine granular precipitate. Isolated precipitate by filtration and washed thoroughly with ethyl acetate (150 mL) to give 3.0 g of product (14).

$^1$H NMR (d$_6$DMSO, 400 MHz): 8.61 (3H, bs), 8.42 (2H, d, J=3.13), 8.26 (2H, d, J=3.13), 7.03 (1H, bs), 6.67 (1H, s), 6.50 (1H, bs), 4.95–5.05 (1H, m), 3.57 (3H, s), 3.00–3.10 (2H, m), 2.56 (3H, s), 2.47 (3H, s), 1.99 (3H, s), 1.97–2.03 (1H, m), 1.82–1.90 (1H, m), 1.40–1.60 (2H, m).

ES MS M+1=454. [$\alpha_D$]=+13.45°, (C=2.52, MeOH).

The invention compounds have demonstrated thrombin inhibitory activity in the standard assays commonly employed by those skilled in the art.

Determination of Thrombin K$_i$

The affinity of inhibitors for thrombin was measured according to the procedures described in (DiMaio, et al., *J. Biol. Chem.*, 1990; 265:21698). Inhibition of amidolytic activity of human thrombin was measured fluorometrically using Tos-Gly-Pro-Arg-AMC as a fluorogenic substrate in 50 mM Tris-HCl buffer (pH 7.52 at 37° C.) containing 0.1 M NaCl and 0.1% poly(ethylene glycol) 8000 at room temperature. Buffer substrate and inhibitor were mixed, and the reaction was initiated by adding the enzyme solution. Initial velocities were recorded at several inhibitor and substrate concentrations. Kinetic parameters were determined by fitting the data to a general equation describing enzyme inhibition (Segel, *Enzyme Kinetics*, Wiley Interscience Publications, 1993).

The hydrolysis of the substrate by thrombin was monitored on a Varian-Cary 2000% spectrophotometer in the fluorescence mode (l$_{ex}$=383 nm, l$_{em}$=455 nm) or on a Hitachi F2000 fluorescence spectrophotometer (l$_{ex}$=383 nm, l$_{em}$=455 nm), and the fluorescent intensity was calibrated using AMC. The reaction reached a steady-state within 3 minutes after mixing thrombin with the substrate and an inhibitor. The steady-state velocity was then measured for a few minutes. The compounds of this invention were also preincubated with thrombin for 20 minutes at room temperature before adding the substrate. The steady-state was achieved within 3 minutes and measured for a few minutes. The kinetic data (the steady-state velocity at various concentrations of the substrate and the inhibitors) of the competitive inhibition was analyzed using the methods described by Segel (1975). A nonlinear regression program, RNLIN in the IMSL library (IMSL, 1987), LMDER in MINPACK library (More, et al., 1980) or Microsoft Excel was used to estimate the kinetic parameters (K$_m$, Vmax and K$_i$).

Determination of Factor Xa IC$_{50}$

The ability of compounds to act as inhibitors of Factor Xa catalytic activity is assessed by determination of that concentration of test substance that inhibits by 50% (IC$_{50}$) the ability of Factor Xa to cleave the chromogenic substrate S2765 (N-CBz-D-Arg-L-Gly-L-Arg-p-nitroanilide•2 HCl). Typically, Factor Xa in 10 mM HEPES, 100 mM NaCl, 0.05% BSA, and 0.1% PEG-8000 and the test substance in DMSO are incubated for 60 minutes at room temperature. To this mixture is added S2765 and the velocity of S2765 hydrolysis measured by observing the intensity of absorbance at 405 nM over 5 minutes.

Determination of Trypsin IC$_{50}$

The ability of compounds to act as inhibitors of trypsin catalytic activity is assessed by determination of that concentration of test substance that inhibits by 50% (IC$_{50}$) the ability of trypsin to cleave the chromogenic substrate S2222 (N-Bz-L-Ile-L-Glu-L-Gly-L-Arg-p-nitroanilide•HCl). Typically, trypsin in 10 mM HEPES, 100 mM NaCl, 0.05% BSA, and 0.1% PEG-8000, and the test substance in DMSO are incubated for 60 minutes at room temperature. To this mixture is added S2222 and the velocity of S2222 hydrolysis measured by observing the intensity of absorbance at 405 nM over 5 minutes.

Arterial Thrombosis Model FeCl$_3$—Induced Carotid Arterial Injury Model

The FeCl$_3$—induced injury to the carotid artery in rats was induced according to the method described by Kurz K. D., Main R. W., Sandusky G. E., *Thrombosis Research*, 1990; 60:269–280 and Schumacher W. A., et al., *J. Pharmacology and Experimental Therapeutics*, 1993; 267:1237–1242.

Male, Sprague-Dawley rats (375–410 g) were anesthetized with urethane (1500 mg/kg ip). Animals were laid on a 37° C. heating pad. The carotid artery was exposed through a midline cervical incision. Careful blunt dissection was used to isolate the vessel from the carotid sheath. Using forceps, the artery was lifted to provide sufficient clearance to insert two small pieces of polyethylene tubing (PE-205) underneath it. A temperature probe (Physitemp MT23/3) was placed between one of the pieces of tubing and the artery. Injury was induced by topical application on the carotid artery above the temperature probe of a small disc (3 mm dia.) of Whatman No. 1 filter paper previously dipped in a 35% solution of FeCl$_3$. The incision area was covered with aluminum foil in order to protect the FeCl$_3$ from degradation by light. The vessel temperature was monitored for 60 minutes after application of FeCl$_3$ as an indication of blood flow. Vessel temperature changes were recorded on a thermistor (Cole-Palmer Model 08533-41).

The time between the FeCl$_3$ application and the time at which the vessel temperature decreased abruptly (>2.4° C.) was recorded as the time to occlusion of the vessel. The fold shift in mean occlusion time (MOT), therefore, refers to the time to occlusion in drug-treated animal divided by control time to occlusion. Inhibitor compounds were given as an IV bolus (0.75 mg/kg) followed immediately by an IV infusion (50 μg/kg/min via femoral vein).

| Compound of Example | Ki Thrombin/nM | IC$_{50}$ Factor Xa/nM | IC$_{50}$ Trypsin/nM | Fold Shift in MOT |
|---|---|---|---|---|
| 11 | 3 | 30 | <1 | >3.3 |

The foregoing biological data establish the compounds of this invention are useful for preventing and treating thrombotic disorders, for example, venous thrombosis, arterial thrombosis, pulmonary embolism, myocardial infarction, and cerebral infarction. The compounds are thus well-suited to formulation for convenient administration to mammals for the prevention and treatment of such disorders. The following examples further illustrate typical formulations provided by the invention.

| Formulation 1 | |
|---|---|
| Ingredient | Amount |
| [6S-[6α[R*(R*)],8aα]]-2-[3-(3,4-Dichloro-phenyl)-propyl]-1,4-dioxo-octahydro-pyrrolo[1,2-a]pyrazine-6-carboxylic acid [2-benzothiazol-2-yl-1-(1-carbamimidoyl-piperidin-3-ylmethyl)-2-oxo-ethyl]-amide | 200 mg |
| Sodium Benzoate | 5 mg |
| Isotonic Saline | 1000 mL |

The above ingredients are mixed and dissolved in the saline for IV administration to a human suffering from, for example, arterial thrombosis.

| Formulation 2 | |
|---|---|
| Ingredient | Amount |
| [6S-[6α(R*),8aα]]-1,4-Dioxo-2-(3-phenyl-propyl)-octahydro-pyrrolo[1,2-a]pyrazine-6-carboxylic acid [1-(3-carbamimidoyl-benzyl)-2-(1-methyl-1H-benzoimidazol-2-yl)-2-oxo-ethyl]-amide | 100 mg |
| Cellulose, Microcrystalline | 400 mg |
| Stearic Acid | 5 mg |
| Silicon Dioxide | 10 mg |
| Sugar, Confectionery | 50 mg |

The ingredients are blended to uniformity and pressed into a tablet that is well-suited for oral administration to a human for preventing, for example, cerebral infarction.

| Formulation 3 | |
|---|---|
| Ingredient | Amount |
| 6S-[6α[R*(trans)),8aα]]-1,4-Dioxo-2-(3-phenyl-propyl)-octahydro-pyrrolo[1,2-a]pyrazine-6-carboxylic acid [2-benzothiazol-2-yl-1-(4-amino-cyclohexyl)-2-oxo-ethyl]-amide | 200 mg |
| Starch, Dried | 250 mg |
| Magnesium Stearate | 10 mg |

The ingredients are combined and milled to afford material suitable for filling hard gelatin capsules administered to humans suffering from, for example, venous thrombosis.

What is claimed is:

1. A compound of the formula

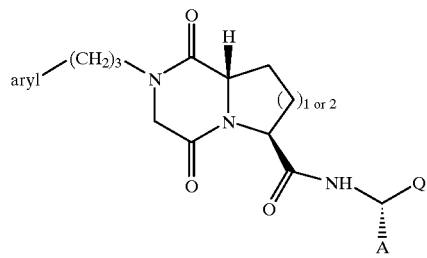

wherein:

A is selected from —(CH$_2$)$_3$—(CH$_2$)$_n$—Y,

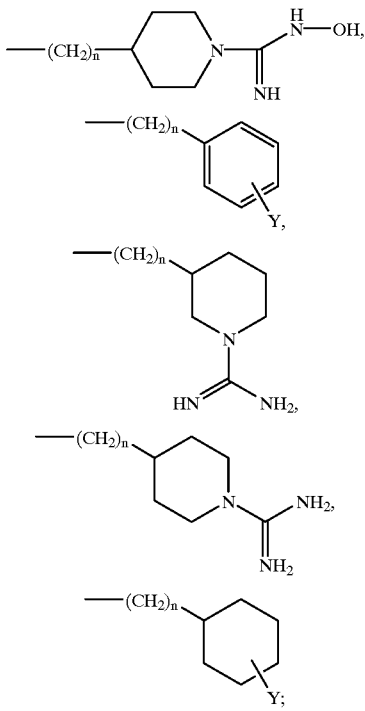

Y is selected from

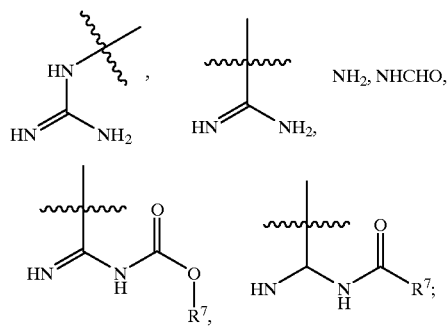

R$^7$ is C$_{1-6}$ alkyl, —(CH$_2$)$_n$-aryl;

Q is selected from

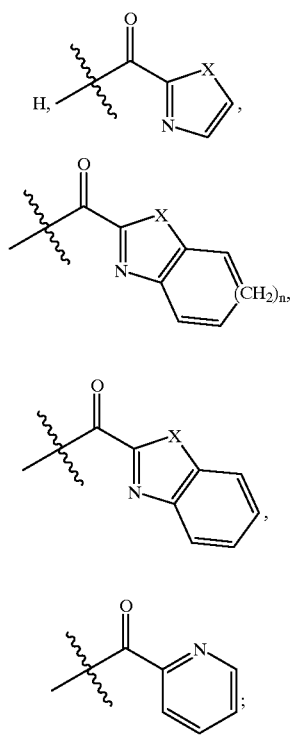

X is NMe, S, or O;

n is selected from 0 to 2;

aryl is naphthyl, phenyl, or phenyl substituted with one, two or three groups selected from halo, hydroxy, $C_1$–$C_6$-alkoxy, SH, $SC_1$–$C_6$ alkyl, $NH_2$, $NHC_1$–$C_6$ alkyl, N di $C_1$–$C_6$ alkyl, CN, and $NO_2$; or pharmaceutically acceptable salts thereof.

2. A compound according to claim 1 wherein A is

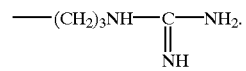

3. A compound according to claim 1 where A is

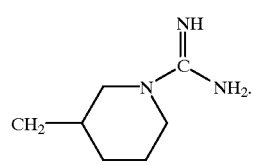

4. A pharmaceutical composition comprising a compound of claim 1 admixed with a inert carrier, diluent, or excipient.

* * * * *